US007867502B1

(12) United States Patent
Andersen et al.

(10) Patent No.: US 7,867,502 B1
(45) Date of Patent: Jan. 11, 2011

(54) TUBERCULOSIS VACCINE AND DIAGNOSTICS BASED ON THE *MYCOBACTERIUM TUBERCULOSIS* SAT-6 GENE FAMILY

(75) Inventors: Peter Andersen, Bronshoj (DK); Rikke Louise Vinther Skjot, Frederiksberg C (DK)

(73) Assignee: Statens Serum Institut, Copenhagen S (DK)

( * ) Notice: Subject to any disclaimer, the term of this patent is extended or adjusted under 35 U.S.C. 154(b) by 823 days.

(21) Appl. No.: 10/723,908

(22) Filed: Nov. 26, 2003

Related U.S. Application Data

(63) Continuation of application No. 09/615,947, filed on Jul. 13, 2000, now abandoned.

(60) Provisional application No. 60/144,011, filed on Jul. 15, 1999.

(30) Foreign Application Priority Data

Jul. 13, 1999 (DK) .............................. 1999 01020

(51) Int. Cl.
*A61K 39/00* (2006.01)
*A61K 39/04* (2006.01)
*A61K 39/02* (2006.01)

(52) U.S. Cl. ...................... 424/248.1; 424/9.1; 424/9.2; 424/184.1; 424/185.1; 424/190.1; 424/192.1; 424/234.1; 530/300; 530/350

(58) Field of Classification Search .................. 424/9.1, 424/9.2, 184.1, 185.1, 190.1, 192.1, 234.1, 424/248.1; 530/300, 350
See application file for complete search history.

(56) References Cited

U.S. PATENT DOCUMENTS 6,555,653 B2 * 4/2003 Alderson et al. ............ 530/350

FOREIGN PATENT DOCUMENTS

WO WO 98/53075 11/1998
WO WO 98/53076 11/1998
WO WO 99/24577 5/1999

OTHER PUBLICATIONS

"Evaluation of the Protective Potency of New Tuberculosis Vaccines", Review of Infectious Diseases, vol. 11, Supplement 2, pp. S484-S490, Mar.-Apr. 1989.*

Ravn et al, Human T cell . . . , Journal of Infectious Diseases 179 (1999), pp. 637-645.

Berthet et al, "A *Mycobacterium tuberculosis* . . . ", Microbiology 144 (1998) pp. 3195-3203.

Cole et al., "Deciphering the biology of . . . ", Nature 393 (Jun. 11, 1998), pp. 537-544.

Andersen et al., "Recall of long . . . ", Journal of Immunology 154 (1995), pp. 3359-3372.

Ulmer et al, "Polynucleotide . . . ", Curr Opin Invest Drugs 2(9) (1993), pp. 983-989.

Flynn et al, "An Essential Role . . . ", J Exp Med 178 (Dec. 1993), pp. 2249-2254.

Cooper et al, "Disseminated . . . ", J Exp Med. 178 (Dec. 1993), pp. 2243-2247.

Andersen et al, "Simultaneous . . . ", J of Immunological Methods 161 (1993), pp. 29-39.

Orme, "Characteristics . . . ", J of Immunology 140(10) (May 15, 1988), pp. 3589-3593.

Seq ID 17 Search report data base rpr result 1, p. 1 (Cole et al.).

Seq ID 17 Search report data base .rspt result 1, p. 1 (Skelton et al.).

GenBank 1998 Accession CAB02330, Cole, S. T. et al.

GenBank 1993 Accession AAA46177, Eberle, R. at al.

Rindi, Laura et al., "Search for genes potentially involved in Mycobacterium tuberculosis virulence by mRNA differential display", Biochemical and Biophysical Research Communications, vol. 258, pp. 94-101, (1999).

* cited by examiner

*Primary Examiner*—Rodney P. Swartz
(74) *Attorney, Agent, or Firm*—Birch, Stewart, Kolasch & Birch, LLP

(57) ABSTRACT

This invention relates to a polypeptide fragment which comprises an amino acid sequence encoded by a member of the esat-6 gene. A member of the esat-6 gene family is defined as gene encoding a small protein and that two such genes are arranged next to each other on the genome and that at least one of the gene products has an amino acid sequence identity to either Rv3874, Rv3875, or Rv0288 of at least 15%.

22 Claims, 6 Drawing Sheets

TUBERCULOSIS VACCINE AND DIAGNOSTICS BASED ON THE *MYCOBACTERIUM TUBERCULOSIS* SAT-6 GENE FAMILY

This application is a continuation of abandoned U.S. patent application Ser. No. 09/615,947, filed on Jul. 13, 2000, the entire contents of which are hereby incorporated by reference. This application also reclaims priority under 35 U.S.C. §120/119 to Danish Application No. PA 1999 01020, filed on Jul. 13, 1999, and U.S. Provisional Patent No. 60/144,011, filed on Jul. 15, 1999.

FIELD OF THE INVENTION

The present invention relates to a number of immunologically active, novel polypeptide fragments derived from the *Mycobacterium tuberculosis*, vaccines and other immunologic compositions containing the fragments as immunogenic components, and methods of production and use of the polypeptides. The invention also relates to novel nucleic acid fragments derived from *M. tuberculosis* which are useful in the preparation of the polypeptide fragments of the invention or in the diagnosis of infection with *M. tuberculosis.*

BACKGROUND OF THE INVENTION

Human tuberculosis caused by *Mycobacterium tuberculosis* is a severe global health problem responsible for approx. 3 million deaths annually, according to the WHO. The worldwide incidence of new TB cases has been progressively falling for the last decade but during the recent years this trend has markedly changed due to the advent of AIDS and the appearance of multidrug resistant strains of *M. tuberculosis.*

The only vaccine presently available for clinical use is BCG, a vaccine which efficacy remains a matter of controversy. BCG generally induces a high level of acquired resistance in animal models of TB, but several human trials in developing countries have failed to demonstrate significant protection. Notably, BCG is not approved by the FDA for use in the United States because BCG vaccination impairs the specificity of the Tuberculin skin test for diagnosis of TB infection.

This makes the development of a new and improved vaccine against TB an urgent matter which has been given a very high priority by the WHO. Many attempts to define protective mycobacterial substances have been made, and from 1950 to 1970 several investigators reported an increased resistance after experimental vaccination. However, the demonstration of a specific long-term protective immune response with the potency of BCG has not yet been achieved.

Immunity to *M. tuberculosis* is characterized by three basic features; 1) Living bacilli efficiently induces a protective immune response; 2) Specifically sensitized T lymphocytes mediate this protection, and 3) The most important mediator molecule seems to be interferon gamma (IFN-$\gamma$).

*M. tuberculosis* holds, as well as secretes, several proteins of potential relevance for the generation of a new tuberculosis (TB) vaccine. For a number of years a major effort has been put into the identification of new protective antigens for the development of a new vaccine against TB. The search for candidate molecules has primarily focused on proteins released from the dividing bacteria. Several molecules have been identified and characterized from this mycobacterial protein fraction. One low molecular mass protein from culture filtrate, ESAT-6, has been found to be an extraordinary potent IFN-$\gamma$ inducer, when used to stimulate human Peripheral Blood Mononuclear Cells (PBMC) from tuberculosis (TB) patients (Ravn et al. 1999).

The total sequencing of the *M. tuberculosis* genome has led to several important findings. A subject of interest was the finding that the potent T-cell antigen ESAT-6 was transcribed together with another low mass protein (CFP10). The genes encoding these two proteins were in other words found next to each other on the mycobacterial genome, located in the same operon and were regulated by the same promoter. The two genes have a sequence identity of approximately 40%. On amino acid level, the sequence identity was approximately 15%. The proteins have approx. same size and pl.

Together with a number of putative Open Reading Frames (ORFs) these two molecules constitute what has been called the esat-6 gene family (Cole et al. 1998, Berthet et al 1998). All the genes in this family encode low mass proteins, which are placed in operon like structures as are ESAT-6 and CFP10. The family was first described by Cole et al. 1998 with the following words: "The potent T-cell antigen ESAT-6, which is probably secreted in a Sec-independent manner, is encoded by a member of a multigene family. Examination of the genetic context reveals several similarly organized operons that include genes encoding large ATP-hydrolysing membrane proteins that might act as transporters." and was later described by Berthet et al. 1998 as follows: "Several genes sharing weak similarities with esat-6 have been previously identified during the *M. tuberculosis* genome sequencing project. Although these genes share less than 35% sequence similarity with each other, they were grouped in the esat-6 gene family since they all potentially code for small polypeptides of about 100 amino acids. All these genes are organized in operon-like structures and are frequently preceded by genes encoding repetitive proteins of the PE and the PPE families".

Diagnosing *M. tuberculosis* in its earliest stage is important for effective treatment of the disease. Current diagnostic assays to determine *M. tuberculosis* infection are expensive and labor intensive. In our part of the world the majority of patients exposed to *M. tuberculosis* receive chest x-rays and attempts are made to culture the bacterium in vitro from sputum samples. X-rays as a diagnostic assay is insensitive and can only identify infections in a very progressed stage. Culturing of *M. tuberculosis* is also not ideal as a diagnostic tool, since the bacteria grows poorly and slowly outside the body, which can produce false negative test results and take weeks before results are obtained. An inexpensive assay, used in third world countries, is the standard tuberculin skin test. It is far from ideal in detecting infection because it cannot distinguish *M. tuberculosis* infected individuals from *M. bovis* BCG vaccinated individuals and therefore cannot be used in areas of the world where patients receive or have received childhood vaccination with bacterial strains related to *M. tuberculosis* (BCG vaccination).

SUMMARY OF THE INVENTION

In the broadest aspect, the present invention relates to a substantially pure polypeptide fragment which comprises an amino acid sequence encoded by a member of the esat-6 gene family or comprises an amino acid analogue having a sequence identity with a polypeptide fragment encoded by a member of the esat-6 gene family of at least 70% and at the same time being immunologically equivalent to the polypeptide fragment encoded by a member of the esat-6 gene family. A member of the esat-6 gene family is defined as gene encoding a small protein and that two such genes are arranged next to each other on the genome and that at least one of the gene products has an amino acid sequence identity to either Rv3874, Rv3875, or Rv0288 of at least 15%. Presently the following genes are members of the esat-6 gene family: Rv0287, Rv0288, Rv1036c, Rv1037c, Rv1038c, Rv1197, Rv1198, Rv1792, Rv1793, Rv2346c, Rv2347c, Rv2348c, Rv2653c, Rv2654c, Rv3019c, Rv3020c, Rv3444c, Rv3445c, Rv3619c, Rv3620c, Rv3874, Rv3875, Rv3890c, Rv3891c, Rv3904c, and Rv3905c.

These proteins have an important mycobacteria specific function which may be related to the intracellular habitat of the macrophage phagosome. Furthermore, they show high immunological efficacy, as described in examples 1, 3a and 3b. They are therefore suggested as useful candidates in a vaccine against TB or diagnostic preparation for TB. The genes encoding these proteins are suggested as components in a DNA vaccine against TB.

DETAILED DISCLOSURE OF THE INVENTION

In the present specification and claims, the term "polypeptide fragment", or variants thereof, denotes both short peptides with a length of at least two amino acid residues and at most 10 amino acid residues, oligopeptides (11-100 amino acid residues), and longer peptides. The polypeptide fragment may be chemically modified by being glycosylated, by being lipidated, or by comprising prosthetic groups.

In the present context the term "substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. free of any other antigen from bacteria belonging to the tuberculosis complex. This can be accomplished by preparing the polypeptide fragment by means of recombinant methods in a non-mycobacterial host cell as will be described in detail below, or by synthesizing the polypeptide fragment by the well-known methods of solid or liquid phase peptide synthesis, e.g. by the method described by Merrifield or variations thereof.

The "tuberculosis-complex" has its usual meaning, i.e. the complex of mycobacteria causing TB which are *Mycobacterium tuberculosis, Mycobacterium bovis, Mycobacterium bovis* BCG, and *Mycobacterium africanum.*

By the term "virulent *Mycobacterium*" is understood a bacterium capable of causing the tuberculosis disease in a mammal including a human being. Examples of virulent *Mycobacteria* are *M. tuberculosis, M. africanum*, and *M. bovis.*

By "a TB patient" is understood an individual with culture or microscopically proven infection with virulent *Mycobacteria*, and/or an individual clinically diagnosed with TB and who is responsive to anti-TB chemotherapy. Culture, microscopy and clinical diagnosis of TB is well known by the person skilled in the art.

By the term "PPD positive individual" is understood an individual with a positive Mantoux test or an individual where PPD induces an increase in in vitro recall response determined by release of IFN-γ of at least 1,000 pg/ml from Peripheral Blood Mononuclear Cells (PBMC) or whole blood, the induction being performed by the addition of 2.5 to 5 μg of PPD/ml to a suspension comprising about 1.0 to $2.5\times10^5$ PBMC, the release of IFN-γ being assessable by determination of IFN-γ in supernatant harvested 5 days after the addition of PPD to the suspension compared to the release of IFN-γ without the addition of PPD.

By the term "delayed type hypersensitivity reaction" is understood a T-cell mediated inflammatory response elicited after the injection of a polypeptide into or application to the skin, said inflammatory response appearing 72-96 hours after the polypeptide injection or application.

By the term "IFN-γ" is understood interferon-gamma.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

The term "sequence identity" indicates a quantitative measure of the degree of homology between two amino acid sequences of equal length or between two nucleotide sequences of equal length. If the two sequences to be compared are not of equal length, they must be aligned to best possible fit. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC($N_{dif}$=2 and $N_{ref}$=8). A gap is counted as non-identity of the specific residue(s), i.e. the DNA sequence AGTGTC will have a sequence identity of 75% with the DNA sequence AGTCAGTC($N_{dif}$=2 and $N_{ref}$=8). Sequence identity can alternatively be calculated by the BLAST program e.g. the BLASTP program (Pearson W. R and D. J. Lipman (1988) PNAS USA 85:2444-2448). In one aspect of the invention, alignment is performed with the global align algorithm with default parameters as described by X. Huang and W. Miller. Adv. Appl. Math. 1991) 12:337-357.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%.

The *M. tuberculosis* antigens provided herein include variants that are encoded by DNA sequences which are substantially homologous to one or more of the DNA sequences specifically recited herein. Sequence identity as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50-60° C., 5×SSC overnight or, in the case of cross-species homology at 45° C., 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

Each polypeptide fragment may thus be characterized by specific amino acid and nucleic acid sequences. It will be understood that such sequences include analogues and variants produced by recombinant methods wherein such nucleic acid and polypeptide sequences have been modified by substitution, insertion, addition and/or deletion of one or more nucleotides in said nucleic acid sequences to cause the substitution, insertion, addition or deletion of one or more amino acid residues in the recombinant polypeptide.

When the term nucleotide is used in the following, for a number of purposes it can be understood as DNA, RNA, PNA or LNA equally. However, as the person skilled in the art will realise, obvious restrictions apply. PNA or LNA may be used instead of DNA. PNA has been shown to exhibit a very dynamic hybridization profile (PNA is described in Nielsen P E et al., 1991, Science 254: 1497-1500). LNA (Locked Nucleic Acids) is a recently introduced oligonucleotide analogue containing bicyclo nucleoside monomers (Koshkin et al., 1998, 54, 3607-3630; Nielsen, N. K. et al. J. Am. Chem. Soc 1998, 120, 5458-5463).

The esat-6 gene family consist of genes, wherein criteria a) through c) below are satisfied:

a) genes coding for small proteins;

b) at least two such genes are arranged next to each other on the genome;

c) at least one of the gene products in criteria b) has an amino acid sequence identity to either Rv3874 (SEQ ID NO: 1), Rv3875 (SEQ ID NO: 2), or Rv0288 (SEQ ID NO: 3) of at least 15%.

One common denominator of the esat-6 family is the small size of the protein products of the genes. In this context, a small protein is about 80 amino acids, e.g. about 90 amino acids, about 100 amino acids, about 110 amino acids, about 120 amino acids, about 130 amino acids, about 140 amino acids, or about 150 amino acids.

These proteins have an important mycobacteria specific function which may be related to the intracellular habitat of the macrophage phagosome and might suggest that the expression of these molecules are synchronously upregulated in a particular phase of the infection during intracellular growth. This upregulation is a possible explanation of the high antigenicity of the proteins in this family. The amino acid sequence identity in criteria c) is preferably more than 15%, such as more than 20%, e.g. more than 25%, 30% or even more than 35%.

Presently, the following genes satisfy criteria a) through c) above and are thus identified members of the esat-6 gene family (see Table 1):

Rv0287, Rv0288 (TB10.4), Rv1036c, Rv1037c, Rv1038c, Rv1197, Rv1198, Rv1792, Rv1793, Rv2346c, Rv2347c, Rv2348c, Rv2653c, Rv2654c, Rv3019c, Rv3020c, Rv3444c, Rv3445c, Rv3619c, Rv3620c, Rv3874 (CFP10), Rv3875 (ESAT-6), Rv3890c, Rv3891c, Rv3904c, and Rv3905c.

As disclosed in example 1, CFP10, ESAT-6, and TB10.4 (previously named CFP7) are exceedingly good IFN-γ inducers, when the purified recombinant antigens are used to stimulate PBMC's from human TB patients. Such an effect (as described in criteria d) ii) below) is an important first test, prior to the determination of whether this protein should be further developed as a component in a vaccine or diagnostic composition. Interestingly, also recombinant Rv1793 and synthetic peptides derived from this protein and from Rv0287, both members of the esat-6 gene family, stimulated T-cell proliferation and IFN-γ production in PBMCs from two PPD-positive donors (WO98/53075 and WO98/53076).

In one embodiment of the present invention, the protein product of a member of the esat-6 family should further satisfy criteria d):

d) At least one of the properties below should be positive:

i) it induces an in vitro response during primary infection with virulent *Mycobacteria*, determined by release of IFN-γ of at least 1,500 pg/ml from T-lymphocytes withdrawn from a mouse within 28 days after the mouse has been infected with $5\times10^{44}$ virulent *Mycobacteria*, the induction being performed by the addition of the polypeptide to a suspension comprising about $2\times10^5$ cells isolated from the spleen, the addition of the polypeptide resulting in a concentration of not more than 20 μg per ml suspension, the release of IFN-γ being assessable by determination of IFN-γ in supernatant harvested 3 days after the addition of the polypeptide to the suspension, ii) it induces in vitro recall response determined by release of IFN-γ of at least 500 pg/ml, preferably 1,000 pg/ml from Peripheral Blood Mononuclear Cells (PBMC) or whole blood withdrawn from TB patients 0-6 months after diagnosis, or PPD positive individuals, the induction being performed by the addition of the polypeptide to a suspension comprising about 1.0 to $2.5\times10^5$ PBMC or whole blood cells, the addition of the polypeptide resulting in a concentration of not more than 20 μg per ml suspension, the release of IFN-γ being assessable by determination of IFN-γ in supernatant harvested 5 days after the addition of the polypeptide to the suspension, iii) it induces a specific antibody response in a TB patient as determined by an ELISA technique or a western blot when the serum is diluted 1:20 in PBS and incubated with the polypeptide in a concentration of at the most 20 μg/ml and induces an OD of at least 0.1 in ELISA, or a visual response in western blot, iv) it induces a positive in vitro response determined by release of IFN-γ of at least 500 pg/ml from Peripheral Blood Mononuclear Cells (PBMC) withdrawn from an individual clinically or subclinically infected with a virulent *Mycobacterium*, the induction being performed by the addition of the polypeptide to a suspension comprising about 1.0 to $2.5\times10^5$ PBMC, the addition of the polypeptide resulting in a concentration of not more than 20 μg per ml suspension, the release of IFN-γ being assessable by determination of IFN-γ in supernatant harvested 5 days after the addition of the polypeptide to the suspension, and preferably does not induce such an IFN-γ release in an individual not infected with a virulent *Mycobacterium*, v) it induces a positive in vitro response determined by release of IFN-γ of at least 500 pg/ml from T cell lines generated from PPD positive individuals, the induction being performed by the addition of the polypeptide to a suspension comprising 1-$5\times10^5$ cells/ml, the addition of the polypeptide resulting in a concentration not more than 20 μg/ml, the release of IFN-γ being assessable by determination of the IFN-γ in supernatant harvested 3-5 days after the addition of the polypeptide to the suspension.

vi) it induces a positive in vitro response determined by T-cell proliferation of at least a stimulation index (SI) of 5 (SI, calculated as mean counts per minute in the presence of antigen divided by the mean counts per minute without antigen) from T cell lines generated from PPD positive individuals, the induction being performed by the addition of the polypeptide to a suspension comprising 1-$5\times10^5$ cells/ml, the addition of the polypeptide resulting in a concentration not more than 20 μg/ml, the release of IFN-γ being assessable by determination of the IFN-γ in supernatant harvested 3-5 days after the addition of the polypeptide to the suspension.

vii) it induces a positive DTH response determined by intradermal injection or local application patch of at most 100 μg of the polypeptide to an individual who is clinically or subclinically infected with a virulent *Mycobacterium*, a positive response having a diameter of at least 10 mm 72-96 hours after the injection or application, viii) it induces a positive DTH response determined by intradermal injection or local application patch of at most 100 μg of the polypeptide to an individual who is clinically or subclinically infected with a virulent *Mycobacterium*, a positive response having a diameter of at least 5 mm 72-96 hours after the injection, and preferably does not induce a such response in an individual who has a cleared infection with a virulent *Mycobacterium.*

The property described in i) will also be satisfied if the release of IFN-γ from reactivated memory T-lymphocytes is 2,000 pg/ml, such as 3,000 pg/ml. In an alternative embodiment of the invention, the immunological effect of the polypeptide could be determined by comparing the IFN-γ release as described with the IFN-γ release from a similar assay, wherein the polypeptide is not added, a significant increase being indicative of an immunologically effective polypeptide. In a preferred embodiment of the invention, the addition of the polypeptide results in a concentration of not more than 20 μg per ml suspension, such as 15 μg, 10 μg, 5 μg, 3 μg, 2 μg, or 1 μg polypeptide per ml suspension.

One example of a mouse strain for property i) is the C57Bl/6j as the animal model. As will be known by a person skilled in the art, due to genetic variation, different strains may react with immune responses of varying strength to the same polypeptide. It is presently unknown which strains of mice will give the best predictability of immunogenic reactivity in which human population. Therefore, it is important to test other mouse strains, such as C3H/HeN, CBA (preferably CBA/J), DBA (preferably DBA/2J), NJ, AKR/N, DBA/1J, FVB/N, SJL/N, 129/SvJ, C3H/HeJ-Lps or BALB mice (preferably BALB/cA, BALB/cJ). It is presently contemplated that also a similar test performed in another animal model such as a guinea pig model or a rat model will have clinical predictability. In order to obtain good clinical predictability to humans, it is contemplated that a model in any farm animal, such as a cow model, a pig model, a deer model, or any primate model will have clinical predictability and thus serve as an animal model.

It should be noted, moreover, that the tuberculosis disease also affects a number of different animal species such as cows, primates, guinea pigs, badgers, possums, and deers. A polypeptide which has proven effective in any of the models mentioned above may be of interest for animal treatment even if it is not effective in a human being.

It is proposed to measure the release of IFN-γ from reactivated T lymphocytes withdrawn from a mouse within 28 days after the mouse has been infected with virulent *Mycobacteria*. This is due to the fact that when an immune host mounts a protective immune response, the specific T-cells responsible for the early recognition of the infected macrophage stimulate a powerful bactericidal activity through their production of IFN-γ (Rook, G. A. W. 1990., Flesch, I. et al. 1987). However, other cytokines could be relevant when monitoring the immunological response to the polypeptide, such as IL-12, TNF-α, IL-4, IL-5, IL-10, IL-6, TGF-β. Usually one or more cytokines will be measured utilising for example the PCR technique or ELISA. It will be appreciated by a person skilled in the art that a significant increase or decrease in the amount of any of these cytokines induced by a specific polypeptide can be used in evaluation of the immunological efficacy of the polypeptide. The ability of a polypeptide to induce a IFN-γ response is presently believed to be the most relevant correlate of protective immunity as mice with a disruption of the gene coding for IFN-γ are unable to control a mycobacterial infection and die very rapidly with widespread dissemination, caseous necrosis and large abcesses (Flynn et al (1993) J. Exp. Med 178: 2249-2254, Cooper et al (1993) J. Exp. Med. 178:2243-2248). A specific model for obtaining information regarding the antigenic targets of a protective immunity in the memory model was originally developed by Lefford (Lefford et al (1973) Immunology 25:703) and has been used extensively in the recent years (Orme et al (1988). Infect. Immun. 140:3589, P. Andersen et al. (1995) J. Immuno 1.154:3359).

The property described in ii) will also be satisfied if the release of IFN-γ from PBMC is determined in PBMC withdrawn from TB patients or PPD positive individuals more than 6 months after diagnosis such as 9 months, 1 year, 2 years, 5 years, or 10 years after diagnosis.

The comments on property i) regarding significant increase in IFN-γ, concentration of polypeptide, and other cytokines are equally relevant to property ii).

The property described in iii) will in particular be satisfied, if the ELISA is performed as follows: the polypeptide of interest in the concentration of 1 to 10 μg/ml is coated on a 96 wells polystyrene plate (NUNC, Denmark) and after a washing step with phosphate buffer pH 7.3, containing 0.37 M NaCl and 0.5% Tween-20 the serum or plasma from a TB patient is applied in dilutions from 1:10 to 1:1000 in PBS with 1% Tween-20. Binding of an antibody to the polypeptide is determined by addition of a labeled (e.g. peroxidase labeled) secondary antibody and reaction is thereafter visualized by the use of OPD and $H_2O_2$ as described by the manufacturer (DAKO, Denmark). The OD value in each well is determined using an appropriate ELISA reader.

In a preferred embodiment, the western blot is performed as follows: The polypeptide is applied in concentrations from 1-40 μg to a SDS-PAGE and after electrophoresis the polypeptide is transferred to a membrane e.g. nitrocellulose or PVDF. The membrane is thereafter washed in phosphate buffer, pH 7.3, containing 0.37 M NaCl and 0.5% Tween-20 for 30 min. The sera obtained from one or more TB patients are diluted 1:10 to 1:1000 in phosphate buffer pH 7.3 containing 0.37 M NaCl. The membrane is hereafter washed four times five minutes in binding buffer and incubated with peroxidase- or phophatase-labeled secondary antibody. Reaction is then visualized using the staining method recommended by the manufacturer (DAKO, Denmark).

The property described in iv) will in particular be satisfied if the polypeptide does not induce such an IFN-γ release in an individual not infected with a virulent *Mycobacterium*, i.e. an individual who has been BCG vaccinated or infected with *Mycobaterium avium* or sensitised by non-tuberculosis *Mycobacterium* or in an individual cleared of an infection with a virulent *Mycobacterium*, i.e. which does not have any positive culture, microscopical or clinical proven ongoing infection with virulent *Mycobacterium*. The comments on property i) regarding significant increase in IFN-γ, concentration of polypeptide, and other cytokines are equally relevant to property iv).

The property described in vii) will in particular be satisfied if the polypeptide does not induce such a response in an individual not infected with a virulent *Mycobacterium*, i.e. an individual who has been BCG vaccinated or infected with *Mycobacterium avium* or sensitised by non-tuberculosis *Mycobacterium*. In a preferred embodiment, the amount of polypeptide intradermally injected or applied is 90 μg, such as 80 μg, 70 μg, 60 μg, 50 μg, 40 μg, or 30 μg. In another embodiment of the invention, the diameter of the positive response is at least 6 mm, such as 7 mm, 8 mm, 9 mm, or 10 mm. In a preferred embodiment, the induration or erythema or both could be determined after administration of the polypeptide by intradermal injection, patch test or multipuncture. The reaction diameter could be positive after more than 48, such as 72 or 96 hours.

The property described in viii) will in particular be satisfied if the polypeptide does not induce such a response in an individual cleared of an infection with a virulent *Mycobacterium*, i.e. which does not have any positive culture or microscopically proven ongoing infection with virulent *Mycobacterium*. The comments on property vii) regarding the amount of polypeptide intradermally injected or applied and the diameter of the positive response are equally relevant to property viii).

One aspect of the present invention relates to a substantially pure polypeptide fragment which comprises an amino acid sequence encoded by a member of the esat-6 gene family having a sequence identity with said polypeptide fragment of at least 70% and at the same time being immunologically equivalent to said polypeptide fragment with the proviso that the substantially pure polypeptide is not selected from the group consisting of Rv0287, Rv0288, Rv1037c, Rv1038c, Rv1197, Rv1198, Rv1792, Rv1793, Rv2347c, Rv2346c, Rv3019c, Rv3619c, Rv3620c, Rv3874, and Rv3875.

In the present context, two polypeptide fragments are immunologically equivalent if they both satisfy property i), property ii), property iii), property iv), property v), property vi), property vii), or property viii).

In both immunodiagnostics and vaccine preparation, it is often possible and practical to prepare antigens from segments of a known immunogenic protein or polypeptide. Certain epitopic regions may be used to produce responses similar to those produced by the entire antigenic polypeptide.

In order to identify relevant T-cell epitopes which are recognized during an immune response, it is also possible to use a "brute force" method: Since T-cell epitopes are linear, deletion mutants of polypeptides having SEQ ID NOs: 5, 7, 9, 11, 13, 15, 17, 19, 21, 23, 25, 27, 29 or 31 will, if constructed systematically, reveal what regions of the polypeptides are essential in immune recognition, e.g. by subjecting these deletion mutants to the IFN-γ assay described herein. Another method utilises overlapping oligopeptides (preferably synthetic having a length of e.g. 20 amino acid residues) derived from polypeptides having SEQ ID NOs: 5, 7, 9, 11, 13, 15, 17, 19, 21, 23, 25, 27, 29 or 31. Some of these will give a positive response in the IFN-γ assay whereas others will not.

In a preferred embodiment of the invention, the polypeptide fragment of the invention comprises an epitope for a B-cell or T-cell.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such

TABLE 1

Tentative list of members of the esat-6 gene family. Proteins coded by adjacent genes are listed together between the lines (e.g. Rv1036c, Rv1037c and Rv1038c). The percentage of identity to TB10.4, CFP10 and ESAT-6, respectively, was calculated according to the LALIGN algorithm used for definition of criteria c) above. SEQ ID NOs are presented in Table 2 (nucleotide sequences) and Table 3 (protein sequences).

| Protein | Size (number of amino acids) | Other names | Percentage of amino acid sequence identity to CFP10 (SEQ ID NO: 1), ESAT-6 (SEQ ID NO: 2), or TB10.4 (SEQ ID NO: 3) |
|---|---|---|---|
| Rv0287 | 97 | | 18.6% (TB10.4), 31.0% (CFP10), 16.5% (ESAT-6) |
| Rv0288 | 96 | TB10.4 (previously named CFP7) | 18.0% (CFP10), 21.9% (ESAT-6) |
| Rv1036c | 112 | | 15.0% (TB10.4), 31.0% (CFP10), 15.0% (ESAT-6) |
| Rv1037c | 94 | | 18.8% (TB10.4), 14.0% (CFP10), 22.1% (ESAT-6) |
| Rv1038c | 98 | | 21.4% (TB10.4), 18.6% (CFP10), 9.2% (ESAT-6) |
| Rv1197 | 98 | | 22.4% (TB10.4), 20.6% (CFP10), 9.2% (ESAT-6) |
| Rv1198 | 94 | | 18.8% (TB10.4), 13.0% (CFP10), 21.1% (ESAT-6) |
| Rv1792 | 98 | | 20.4% (TB10.4), 19.6% (CFP10), 11.2% (ESAT-6) |
| Rv1793 | 94 | | 18.0% (TB10.4), 12.0% (CFP10), 21.2% (ESAT-6) |
| Rv2346c | 94 | | 19.8% (TB10.4), 13.0% (CFP10), 20% (ESAT-6) |
| Rv2347c | 98 | | 21.4% (TB10.4), 18.6% (CFP10), 10.2% (ESAT-6) |
| Rv2348c | 108 | | 14.8% (TB10.4), 13.0% (CFP10), 13% (ESAT-6) |
| Rv2653c | 107 | | 18.3% (TB10.4), 16.5% (CFP10), 16.7% (ESAT-6) |
| Rv2654c | 81 | | 21.0% (TB10.4), 16.0% (CFP10), 20.0% (ESAT-6) |
| Rv3019c | 96 | | 84.4% (TB10.4), 17.0% (CFP10), 24.0% (ESAT-6) |
| Rv3020c | 97 | | 17.5% (TB10.4), 31% (CFP10), 15.5% (ESAT-6) |
| Rv3444c | 100 | | 20% (TB10.4), 15.2% (CFP10), 22.0% (ESAT-6) |
| Rv3445c | 125 | | 15.2% (TB10.4), 12.8% (CFP10), 15.1% (ESAT-6) |
| Rv3619c | 94 | | 18.8% (TB10.4), 14.0% (CFP10), 22.1% (ESAT-6) |
| Rv3620c | 98 | | 21.4% (TB10.4), 19.6% (CFP10), 10.2% (ESAT-6) |
| Rv3874 | 100 | CFP10 | 18.0% (TB10.4), 15.0% (ESAT-6) |
| Rv3875 | 95 | ESAT-6 | 21.9% (TB10.4), 15.0% (CFP10) |
| Rv3890c | 95 | | 25.8% (TB10.4), 18.6% (CFP10), 15.6% (ESAT-6) |
| Rv3891c | 107 | | 23.4% (TB10.4), 16.2% (CFP10), 16.8% (ESAT-6) |
| Rv3904c | 90 | | 23.2% (TB10.4), 19.8% (CFP10), 18.9% (ESAT-6) |
| Rv3905c | 103 | | 22.3% (TB10.4), 21.4% (CFP10), 18.4% (ESAT-6) |

as at least 8, at least 9, at least 10, at least 12, at least 14, at least 16, at least 18, at least 20, at least 22, at least 24, and at least 30 amino acid residues.

In one preferred embodiment, the polypeptide fragment of the invention is free from any signal sequence; this is especially interesting when the polypeptide fragment is produced synthetically but even when the polypeptide fragments are produced recombinantly it is normally acceptable that they are not exported by the host cell to the periplasm or the extracellular space; the polypeptide fragments can be recovered by traditional methods (cf. the discussion below) from the cytoplasm after disruption of the host cells, and if there is need for refolding of the polypeptide fragments, general refolding schemes can be employed, cf. e.g. the disclosure in WO 94/18227 where such a general applicable refolding method is described.

By producing fusion polypeptides, superior characteristics of the polypeptide fragments of the invention can be achieved. For instance, fusion partners which facilitate export of the polypeptide when produced recombinantly, fusion partners which facilitate purification of the polypeptide, and fusion partners which enhance the immunogenicity of the polypeptide fragment of the invention are all interesting possibilities. Therefore, the invention also pertains to a fusion polypeptide comprising at least one polypeptide fragment defined above and at least one fusion partner. The fusion partner can, in order to enhance immunogenicity, e.g. be selected from the group consisting of another polypeptide fragment as defined above (so as to allow for multiple expression of relevant epitopes), and another polypeptide derived from a bacterium belonging to the tuberculosis complex, such as ESAT-6, TB10.4, CFP10, CFP17, CFP21, CFP25, CFP29, MPB59, MPT59, MPB64, and MPT64 or at least one T-cell epitope of any of these antigens. Other immunogenicity enhancing polypeptides which could serve as fusion partners are T-cell epitopes (e.g. derived from the polypeptides ESAT-6, MPB64, MPT64, or MPB59) or other immunogenic epitopes enhancing the immunogenicity of the target gene product, e.g. lymphokines such as IFN-γ, IL-2 and IL-12. In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; gluthatione S-transferase; β-galac-tosidase; or poly-histidine.

Other interesting fusion partners are polypeptides which are lipidated causing that the immunogenic polypeptide is presented in a suitable manner to the immune system. This effect is e.g. known from vaccines based on the *Borrelia burgdorferi* OspA polypeptide, wherein the lipidated membrane anchor in the polypeptide confers a self-adjuvating effect to the polypeptide (which is natively lipidated) when isolated from cells producing it. In contrast, the OspA polypeptide is relatively silent immunologically when prepared without the lipidation anchor.

Another part of the invention pertains to a nucleic acid fragment in isolated form which 1) comprises a nucleic acid sequence which is a member of the esat-6 gene family, and/or
2) has a length of at least 10 nucleotides and hybridizes readily under stringent hybridization conditions (as defined in the art, i.e. 5-10° C. under the melting point $T_m$, cf. Sambrook et al, 1989, pages 11.45-11.49) with a nucleic acid fragment of 1) and/or
3) has a length of at least 10 nucleotides and hybridizes readily under stringent hybridization conditions (as defined in the art, i.e. 5-10° C. under the melting point $T_m$, cf. Sambrook et al, 1989, pages 11.45-11.49) with a nucleic acid fragment which has a nucleotide sequence selected from SEQ ID NO: 6 or a sequence complementary thereto, SEQ ID NO: 12 or a sequence complementary thereto, SEQ ID NO: 14 or a sequence complementary thereto, SEQ ID NO: 16 or a sequence complementary thereto, SEQ ID NO: 18 or a sequence complementary thereto, SEQ ID NO: 20 or a sequence complementary thereto, SEQ ID NO: 22 or a sequence complementary thereto, SEQ ID NO: 24 or a sequence complementary thereto, SEQ ID NO: 26 or a sequence complementary thereto, SEQ ID NO: 28 or a sequence complementary thereto, or SEQ ID NO: 30 or a sequence complementary thereto.

It is preferred that the nucleic acid fragment is a DNA fragment.

To provide certainty of the advantages in accordance with the invention, the preferred nucleic acid sequence when employed for hybridization studies or assays includes sequences that are complementary to at least a 10 to 40, or so, nucleotide stretch of the selected sequence. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained.

Hence, the term "subsequence" when used in connection with the nucleic acid fragments of the invention is intended to indicate a continuous stretch of at least 10 nucleotides which exhibits the above hybridization pattern. Normally, this will require a minimum sequence identity of at least 70% with a subsequence of the hybridization partner having SEQ ID NO: 6, 12, 14, 16, 18, 20, 22, 24, 26, 28 or 30. It is preferred that the nucleic acid fragment is longer than 10 nucleotides, such as at least 15, at least 20, at least 25, at least 30, at least 35, at least 40, at least 45, at least 50, at least 55, at least 60, at least 65, at least 70, and at least 80 nucleotides long, and the sequence identity should preferable also be higher than 70%, such as at least 75%, at least 80%, at least 85%, at least 90%, at least 92%, at least 94%, at least 96%, and at least 98%. It is most preferred that the sequence identity is 100%. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

It is well known that the same amino acid may be encoded by various codons, the codon usage being related, inter alia, to the preference of the organisms in question expressing the nucleotide sequence. Thus, at least one nucleotide or codon of a nucleic acid fragment of the invention may be exchanged by others which, when expressed, result in a polypeptide identical or substantially identical to the polypeptide encoded by the nucleic acid fragment in question. The invention thus allows for variations in the sequence such as substitution, insertion (including introns), addition, deletion and rearrangement of one or more nucleotides, which variations do not have any substantial effect on the polypeptide encoded by the nucleic acid fragment or a subsequence thereof. The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "rearrangement" is intended to mean that two or more nucleotide residues have been exchanged with each other.

The nucleotide sequence to be modified may be of cDNA or genomic origin as discussed above, but may also be of synthetic origin. Furthermore, the sequence may be of mixed cDNA and genomic, mixed cDNA and synthetic or genomic and synthetic origin as discussed above. The sequence may have been modified, e.g. by site-directed mutagenesis, to result in the desired nucleic acid fragment encoding the desired polypeptide. The following discussion focused on modifications of nucleic acid encoding the polypeptide should be understood to encompass also such possibilities, as well as the possibility of building up the nucleic acid by ligation of two or more DNA fragments to obtain the desired nucleic acid fragment, and combinations of the above-mentioned principles.

The nucleotide sequence may be modified using any suitable technique which results in the production of a nucleic acid fragment encoding a polypeptide of the invention.

The modification of the nucleotide sequence encoding the amino acid sequence of the polypeptide of the invention should be one which does not impair the immunological function of the resulting polypeptide.

A preferred method of preparing variants of the antigens disclosed herein is site-directed mutagenesis. This technique is useful in the preparation of individual peptides, or biologically functional equivalent proteins or peptides, derived from the antigen sequences, through specific mutagenesis of the underlying nucleic acid. The technique further provides a ready ability to prepare and test sequence variants, for example, incorporating one or more of the foregoing considerations, by introducing one or more nucleotide sequence changes into the nucleic acid. Site-specific mutagenesis allows the production of mutants through the use of specific oligonucleotide sequences which encode the nucleotide sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, site-directed mutagenesis in accordance herewith is performed by first obtaining a single-stranded vector which includes within its sequence a nucleic acid sequence which encodes the polypeptides of the invention. An oligonucleotide primer bearing the desired mutated sequence is prepared, generally synthetically, e.g. by the method of Crea et al. (1978). This primer is then annealed with the single-stranded vector and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected nucleic acid fragments of the invention using site-directed mutagenesis is provided as a means of producing potentially useful species of the genes and is not meant to be limiting, as there are other ways in which sequence variants of the nucleic acid fragments of the invention may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

The invention also relates to a replicable expression vector which comprises a nucleic acid fragment defined above, especially a vector which comprises a nucleic acid fragment encoding a polypeptide fragment of the invention.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated.

Expression vectors may be constructed to include any of the DNA segments disclosed herein. Such DNA might encode an antigenic protein specific for virulent strains of mycobacteria or even hybridization probes for detecting mycobacteria nucleic acids in samples. Longer or shorter DNA segments could be used, depending on the antigenic protein desired. Epitopic regions of the proteins expressed or encoded by the disclosed DNA could be included as relatively short segments of DNA. A wide variety of expression vectors is possible including, for example, DNA segments encoding reporter gene products useful for identification of heterologous gene products and/or resistance genes such as antibiotic resistance genes which may be useful in identifying transformed cells.

The vector of the invention may be used to transform cells so as to allow propagation of the nucleic acid fragments of the invention or so as to allow expression of the polypeptide fragments of the invention. Hence, the invention also pertains to a transformed cell harbouring at least one such vector according to the invention. Such a transformed cell (which is also a part of the invention) may be any suitable bacterial host cell or any other type of cell such as a unicellular eukaryotic organism, a fungus or yeast, or a cell derived from a multicellular organism, e.g. an animal or a plant. It is especially in cases where glycosylation is desired that a mammalian cell is used, although glycosylation of proteins is a rare event in prokaryotes. Normally, however, a prokaryotic cell is preferred such as a bacterium belonging to the genera *Mycobacterium, Salmonella, Pseudomonas, Bacillus* and *Eschericia*. It is preferred that the transformed cell is an *E. coli, B. subtilis*, or *M. bovis* BCG cell, and it is especially preferred that the transformed cell expresses a polypeptide according to the invention. The latter opens for the possibility to produce the polypeptide of the invention by simply recovering it from the culture containing the transformed cell. In the most preferred embodiment of this part of the invention the transformed cell is *Mycobacterium bovis* BCG strain: Danish 1331, which is the *Mycobacterium bovis* strain Copenhagen from the Copenhagen BCG Laboratory, Statens Seruminstitut, Denmark.

The nucleic acid fragments of the invention allow for the recombinant production of the polypeptides fragments of the invention. However, also isolation from the natural source is a way of providing the polypeptide fragments as is peptide synthesis.

Therefore, the invention also pertains to a method for the preparation of a polypeptide fragment of the invention, said method comprising inserting a nucleic acid fragment as defined above into a vector which is able to replicate in a host cell, introducing the resulting recombinant vector into the host cell (transformed cells may be selected using various techniques, including screening by differential hybridization, identification of fused reporter gene products, resistance markers, anti-antigen antibodies and the like), culturing the host cell in a culture medium under conditions sufficient to effect expression of the polypeptide (of course the cell may be cultivated under conditions appropriate to the circumstances, and if DNA is desired, replication conditions are used), and recovering the polypeptide from the host cell or culture medium; or isolating the polypeptide from whole mycobacteria of the tuberculosis complex or from lysates or fractions thereof, e.g. cell wall containing fractions, or synthesizing the polypeptide by solid or liquid phase peptide synthesis.

The medium used to grow the transformed cells may be any conventional medium suitable for the purpose. A suitable vector may be any of the vectors described above, and an appropriate host cell may be any of the cell types listed above. The methods employed to construct the vector and effect introduction thereof into the host cell may be any method known for such purposes within the field of recombinant DNA. In the following, a more detailed description of the possibilities will be given:

In general, of course, prokaryotes are preferred for the initial cloning of nucleic sequences of the invention and constructing the vectors useful in the invention. For example, in addition to the particular strains mentioned in the more specific disclosure below, one may mention, by way of example, strains such as *E. coli* K12 strain 294 (ATCC No. 31446), *E. coli* B, and *E. coli* X 1776 (ATCC No. 31537). These examples are, of course, intended to be illustrative rather than limiting.

Prokaryotes are also preferred for expression. The aforementioned strains, as well as *E. coli* W3110 (F—, lambda-, prototrophic, ATCC No. 273325), bacilli such as *Bacillus subtilis*, or other enterobacteriaceae such as *Salmonella typhimurium* or *Serratia marcescens*, and various *Pseudomonas* species may be used. Especially interesting are rapid-growing mycobacteria, e.g. *M. smegmatis*, as these bacteria have a high degree of resemblance with mycobacteria of the tuberculosis complex and therefore stand a good chance of reducing the need of performing post-translational modifications of the expression product. In one aspect of the invention it is preferred to produce the polypeptide of the invention in a GRAS organism e.g. *lactococcus*.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977, Gene 2: 95). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used promoter, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

After the recombinant preparation of the polypeptide according to the invention, the isolation of the polypeptide may for instance be carried out by affinity chromatography (or other conventional biochemical procedures based on chromatography), using a monoclonal antibody which substantially specifically binds the polypeptide according to the invention. Another possibility is to employ the simultaneous electroelution technique described by Andersen et al. in J. Immunol. Methods 161: 29-39.

According to the invention, the post-translational modifications may involve lipidation, gly-cosylation, cleavage, or elongation of the polypeptide.

In certain aspects, the DNA sequence information provided by this invention allows for the preparation of relatively short DNA (or RNA, PNA, or LNA) sequences having the ability to specifically hybridize to mycobacterial gene sequences. In these aspects, nucleic acid probes of an appropriate length are prepared based on a consideration of the relevant sequence. The ability of such nucleic acid probes to specifically hybridize to the mycobacterial gene sequences lends them particular utility in a variety of embodiments. Most importantly, the probes can be used in a variety of diagnostic assays for detecting the presence of pathogenic organisms in a given sample. However, either use is envisioned, including the use of the sequence information for the preparation of mutant species primers, or primers for use in preparing other genetic constructs.

Apart from their use as starting points for the synthesis of polypeptides of the invention and for hybridization probes (useful for direct hybridization assays or as primers in e.g. PCR or other molecular amplification methods), the nucleic acid fragments of the invention may be used for effecting in vivo expression of antigens, i.e. the nucleic acid fragments may be used in so-called DNA vaccines. Recent research have revealed that a DNA fragment cloned in a vector which is non-replicative in eukaryotic cells may be introduced into an animal (including a human being) by e.g. intramuscular injection or percutaneous administration (the so-called "gene gun" approach). The DNA is taken up by e.g. muscle cells and the gene of interest is expressed by a promoter which is functioning in eukaryotes, e.g. a viral promoter, and the gene product thereafter stimulates the immune system. These newly discovered methods are reviewed in Ulmer et al., 1993, which hereby is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections with mycobacteria of the tuberculosis complex in an animal, including a human being.

The efficacy of such a "DNA vaccine" can possibly be enhanced by administering the gene encoding the expression product together with a DNA fragment encoding a polypeptide which has the capability of modulating an immune response. For instance, a gene encoding lymphokine precursors or lymphokines (e.g. IFN-γ, IL-2, or IL-12) could be administered together with the gene encoding the immunogenic protein, either by administering two separate DNA fragments or by administering both DNA fragments included in the same vector. It also is a possibility to administer DNA fragments comprising a multitude of nucleotide sequences which each encode relevant epitopes of the polypeptides disclosed herein so as to effect a continuous sensitization of the immune system with a broad spectrum of these epitopes.

As explained above, the polypeptide fragments of the invention are excellent candidates for vaccine constituents or for constituents in an immune diagnostic agent.

Thus, another part of the invention pertains to an immunologic composition comprising a polypeptide or fusion polypeptide according to the invention. In order to ensure optimum performance of such an immunologic composition it is preferred that it comprises an immunologically and pharmaceutically acceptable carrier, vehicle or adjuvant. Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyl-dioctadecylammonium bromide (DDA), Quil A, poly I:C, Freund's incomplete adjuvant, IFN-γ, IL-2, IL-12, monophosphoryl lipid A (MPL), and muramyl dipeptide (MDP).

A preferred immunologic composition according to the present invention comprises at least two different polypeptide fragments, each different polypeptide fragment being a polypeptide or a fusion polypeptide defined above. It is preferred that the immunologic composition comprises between 2-20, such as 3-20 different polypeptide fragments or fusion poly-peptides.

Such an immunologic composition may preferably be in the form of a vaccine or in the form of a skin test reagent.

In line with the above, the invention therefore also pertain to a method for producing an immunologic composition according to the invention, the method comprising preparing, synthesizing or isolating a polypeptide according to the invention, and solubilizing or dispersing the polypeptide in a medium for a vaccine, and optionally adding other *M. tuberculosis* antigens and/or a carrier, vehicle and/or adjuvant substance.

Preparation of Vaccines which Contain Peptide Sequences as Active Ingredients is Generally well understood in the art, as exemplified by U.S. Pat. Nos. 4,608,251; 4,601,903; 4,599,231 and 4,599,230, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10-95% of active ingredient, preferably 25-70%.

The proteins may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

Some of the polypeptides of the vaccine are sufficiently immunogenic in a vaccine, but for some of the others the immune response will be enhanced if the vaccine further comprises an adjuvant substance.

Various methods of achieving adjuvant effect for the vaccine include use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° C. to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. According to the invention, DDA (dimethyldioctadecylammonium bromide) is an interesting candidate for an adjuvant, but also Freund's incomplete adjuvants as well as QuilA are interesting possibilities. Further possibilities are monophosphoryl lipid A (MPL), and muramyl dipeptide (MDP).

Another highly interesting (and thus, preferred) possibility of achieving adjuvant effect is to employ the technique described in Gosselin et al., 1992 (which is hereby incorporated by reference herein). In brief, the presentation of a relevant antigen such as an antigen of the present invention can be enhanced by conjugating the antigen to antibodies (or antigen binding antibody fragments) against the Fcγ receptors on monocytes/macrophages. Especially conjugates between antigen and anti-FcγRI have been demonstrated to enhance immunogenicity for the purposes of vaccination.

Other possibilities involve the use of immune modulating substances such as lymphokines (e.g. IFN-γ, IL-2 and IL-12) or synthetic IFN-γ inducers such as poly I:C in combination with the above-mentioned adjuvants. As discussed in example 3b, it is contemplated that such mixtures of antigen and adjuvant will lead to superior vaccine formulations.

In many instances, it will be necessary to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain the desired levels of protective immunity. The course of the immunisation may be followed by in vitro proliferation assays of PBMC co-cultured with one or more of the polypeptides members used in the vaccine, e.g. co-culture with ESAT-6 or ST-CF, and especially by measuring the levels of IFN-γ released from the primed lymphocytes. The assays may be performed using conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

Due to genetic variation, different individuals may react with immune responses of varying strength to the same polypeptide. Therefore, the vaccine according to the invention may comprise several different polypeptides in order to increase the immune response. The vaccine may comprise two or more polypeptides, where all of the polypeptides are as defined above, or some but not all of the peptides may be derived from a bacterium belonging to the *M. tuberculosis* complex. In the latter example, the polypeptides not necessarily fulfilling the criteria set forth above for polypeptides may either act due to their own immunogenicity or merely act as adjuvants. Examples of such interesting polypeptides are ESAT-6, TB10.4, and MPT64, but any other substance which can be isolated from mycobacteria are possible candidates.

The vaccine may comprise 1-20, such as 2-20 or even 3-20 different polypeptides, such as 3-10 different polypeptides.

One reason for admixing the polypeptides of the invention with an adjuvant is to effectively activate a cellular immune response. However, this effect can also be achieved in other ways, for instance by expressing the effective antigen in a vaccine in a non-pathogenic microorganism. A well-known example of such a microorganism is *Mycobacterium bovis* BCG.

Therefore, another important aspect of the present invention is an improvement of the living BCG vaccine presently available, which is a vaccine for immunizing an animal, including a human being, against TB caused by mycobacteria belonging to the tuberculosis-complex, comprising as the effective component a microorganism, wherein one or more copies of a DNA sequence encoding a polypeptide as defined above has been incorporated into the genome of the microorganism in a manner allowing the microorganism to express and secrete the polypeptide.

In the present context, the term "genome" refers to the chromosome of the microorganisms as well as extrachromosomally DNA or RNA, such as plasmids. It is, however, preferred that the DNA sequence of the present invention has been introduced into the chromosome of the non-pathogenic microorganism, since this will prevent loss of the genetic material introduced.

It is preferred that the non-pathogenic microorganism is a bacterium, e.g. selected from the group consisting of the genera *Mycobacterium, Salmonella, Pseudomonas* and *Eschericia.* It is especially preferred that the non-pathogenic microorganism is *Mycobacterium bovis* BCG, such as *Mycobacterium bovis* BCG strain: Danish 1331.

The incorporation of one or more copies of a nucleotide sequence encoding the polypeptide according to the invention in a *Mycobacterium* from a *M. bovis* BCG strain will enhance the immunogenic effect of the BCG strain. The incorporation of more than one copy of a nucleotide sequence of the invention is contemplated to enhance the immune response even more, and consequently an aspect of the invention is a vaccine wherein at least 2 copies of a DNA sequence encoding a polypeptide is incorporated in the genome of the microorganism, such as at least 5 copies. The copies of DNA sequences may either be identical encoding identical polypeptides or be variants of the same DNA sequence encoding identical or homologues of a polypeptide, or in another embodiment be different DNA sequences encoding different polypeptides where at least one of the polypeptides is according to the present invention.

The living vaccine of the invention can be prepared by cultivating a transformed non-pathogenic cell according to the invention, and transferring these cells to a medium for a vaccine, and optionally adding a carrier, vehicle and/or adjuvant substance.

The invention also relates to a method of diagnosing TB caused by *Mycobacterium tuberculosis, Mycobacterium africanum* or *Mycobacterium bovis* in an animal, including a human being, comprising intradermally injecting, in the animal, a polypeptide according to the invention or a skin test reagent described above, a positive skin response at the location of injection being indicative of the animal having TB, and a negative skin response at the location of injection being indicative of the animal not having TB. A positive response is a skin reaction having a diameter of at least 5 mm, but larger reactions are preferred, such as at least 1 cm, 1.5 cm, and at least 2 cm in diameter. The composition used as the skin test reagent can be prepared in the same manner as described for the vaccines above.

In line with the disclosure above pertaining to vaccine preparation and use, the invention also pertains to a method for immunizing an animal, including a human being, against TB caused by mycobacteria belonging to the tuberculosis complex, comprising administering to the animal the polypeptide of the invention, or a vaccine composition of the invention as described above, or a living vaccine described above. Preferred routes of administration are the parenteral (such as intravenous and intraarterially), intraperitoneal, intramuscular, subcutaneous, intradermal, oral, buccal, sublingual, nasal, rectal or transdermal route.

A number of possible diagnostic assays and methods can be envisaged:

When diagnosis of previous or ongoing infection with virulent mycobacteria is the aim, a blood sample comprising mononuclear cells (i.e. T-lymphocytes) from a patient could be contacted with a sample of one or more polypeptides of the invention. This contacting can be performed in vitro and a positive reaction could e.g. be proliferation of the T-cells or release of cytokines such as γ-interferon into the extracellular phase (e.g. into a culture supernatant); a suitable in vivo test would be a skin test as described above. It is also conceivable to contact a serum sample from a subject to contact with a polypeptide of the invention, the demonstration of a binding between antibodies in the serum sample and the polypeptide being indicative of previous or ongoing infection.

The invention therefore also relates to an in vitro method for diagnosing ongoing or previous sensitization in an animal or a human being with bacteria belonging to the tuberculosis complex, the method comprising providing a blood sample from the animal or human being, and contacting the sample from the animal with the polypeptide of the invention, a significant release into the extracellular phase of at least one cytokine by mononuclear cells in the blood sample being indicative of the animal being sensitised. By the term "significant release" is herein meant that the release of the cytokine being significantly larger (with a 95% confidence interval as defined by appropriate statistical analysis such as a Student's two-tailed T test) than the cytokine release from a blood sample derived from a patient without the TB diagnosis. Normally, a significant release is at least two times the release observed from such a sample.

Alternatively, a sample of a possibly infected organ may be contacted with an antibody raised against a polypeptide of the invention. The demonstration of the reaction by means of methods well-known in the art between the sample and the antibody will be indicative of an ongoing infection. It is of course also a possibility to demonstrate the presence of anti-mycobacterial antibodies in serum by contacting a serum sample from a subject with at least one of the polypeptide fragments of the invention and using well-known methods for visualizing the reaction between the antibody and antigen.

Also a method of determining the presence of mycobacterial nucleic acids in an animal, including a human being, or in a sample, comprising administering a nucleic acid fragment of the invention to the animal or incubating the sample with the nucleic acid fragment of the invention or a nucleic acid fragment complementary thereto, and detecting the presence of hybridized nucleic acids resulting from the incubation (by using the hybridization assays which are well-known in the art), is also included in the invention. Such a method of diagnosing TB might involve the use of a composition comprising at least a part of a nucleotide sequence as defined above and detecting the presence of nucleotide sequences in a sample from the animal or human being to be tested which hybridize with the nucleic acid fragment (or a complementary fragment) by the use of PCR technique.

The fact that certain of the disclosed antigens are not present in *M. bovis* BCG but are present in virulent mycobacteria point them out as interesting drug targets; the antigens may constitute receptor molecules or toxins which facilitate the infection by the *Mycobacterium*, and if such functionalities are blocked the infectivity of the *Mycobacterium* will be diminished.

To determine particularly suitable drug targets among the antigens of the invention, the gene encoding at least one of the polypeptides of the invention and the necessary control sequences can be introduced into a virulent strains of mycobacteria (e.g. BCG) so as to determine which of the polypeptides are critical for virulence. Once particular proteins are identified as critical for/contributory to virulence, anti-mycobacterial agents can be designed rationally to inhibit expression of the critical genes or to attack the critical gene products. For instance, antibodies or fragments thereof (such as Fab and $(Fab')_2$ fragments can be prepared against such critical polypeptides by methods known in the art and thereafter used as prophylactic or therapeutic agents. Alternatively, small molecules can be screened for their ability to selectively inhibit expression of the critical gene products, e.g. using recombinant expression systems which include the gene's endogenous promoter, or for their ability to directly interfere with the action of the target. These small molecules are then used as therapeutics or as prophylactic agents to inhibit mycobacterial virulence.

Alternatively, anti-mycobacterial agents which render a virulent *Mycobacterium* a virulent can be operably linked to expression control sequences and used to transform a virulent *Mycobacterium*. Such anti-mycobacterial agents inhibit the replication of a specified *Mycobacterium* upon transcription or translation of the agent in the *Mycobacterium*. Such a "newly a virulent" *Mycobacterium* would constitute a superb alternative to the above described modified BCG for vaccine purposes since it would be immunologically very similar to a virulent *Mycobacterium* compared to e.g. BCG.

Finally, a monoclonal or polyclonal antibody, which is specifically reacting with a polypeptide of the invention in an immuno assay, or a specific binding fragment of said antibody, is also a part of the invention. The production of such polyclonal antibodies requires that a suitable animal be immunized with the polypeptide and that these antibodies are subsequently isolated, suitably by immune affinity chromatography. The production of monoclonals can be effected by methods well-known in the art, since the present invention provides for adequate amounts of antigen for both immunization and screening of positive hybridomas.

REFERENCES

Andersen, P., and I, Heron. 1993. Journal of Immunological Methods 161 29-39

Andersen, P., A. B. Andersen, A. L. Sorensen, and S. Nagai. 1995. J. Immunol. 154:3359-3372.

Berthet, F. X., Rasmussen, P. B., Rosenkrands, I., Andersen, P. Gicquel, B. *Microbiology* (1998)144 3195-3203

S. T. Cole, et al (1998). Nature 393 (6685) 537-544. Ravn et al (1999). J. Infect. Dis. 179, 637-645

WO98/53075

WO98/53076

Rook, G. A. W. (1990). Res. Microbiol. 141:253-256

Flesch, I. et al. (1987). J. Immunology, 138: 4408-4413

Flynn et al (1993) J. Exp. Med 178: 2249-2254,

Cooper et al (1993) J. Exp. Med. 178:2243-2248

Orme et al (1988). Infect. Immun. 140:3589,

Ulmer et al., (1993). Curr. Opin. Invest. Drugs, 2: 983-989

Gosselin et al., (1992) J. Immunol. 149: 3477-3481.

Pearson W. R and D. J. Lipman (1988) PNAS USA 85:2444-2448

X. Huang and W. Miller. Adv. Appl. Math. (1991) 12:337-357

Nielsen P E et al. (1991. Science 254: 1497-1500
Koshkin et al. (1998). Tetrahedron 54, 3607-3630;
Nielsen, N. K. et al. (1998). J. Am. Chem. Soc. 120, 5458-5463
Lefford et al (1973). Immunology 25:703
Crea et al. (1978). PNAS 75(12):5765-5769.
Eichenlaub, (1979). Journal of Bacteriology, 138: 559-566.
Bolivar et al., (1977). Gene 2: 95
Chang et al., (1978). Nature, 375: 515
Itakura et al., (1977). Science, 198: 1056
Goeddel et al., (1979). Nature, 281:544
EPO Appl. Publ. No. 0036776
Siebwenlist et al., (1980). Cell, 20: 269
Harboe et al (1998). Infect. Immun. 66, 717-723
Sambrook et. al. (1989)"Molecular cloning: a laboratory manual, 2nd edition Cold Spring Habor N.Y."
WO 98/44119
WO 94/18227
U.S. Pat. No. 4,603,102
U.S. Pat. No. 4,608,251
U.S. Pat. No. 4,601,903
U.S. Pat. No. 4,599,231
U.S. Pat. No. 4,599,230
U.S. Pat. No. 3,791,932
U.S. Pat. No. 4,174,384
U.S. Pat. No. 3,949,064

Figure 1:
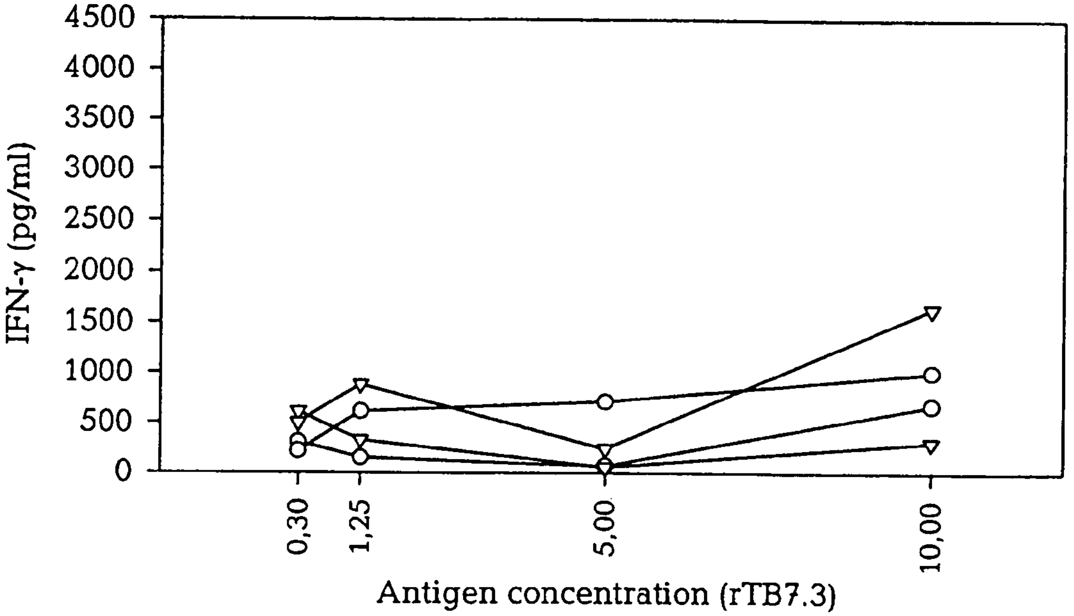
FIGS. 1*a*, 1*b* and 1*c*.
Figure 1:
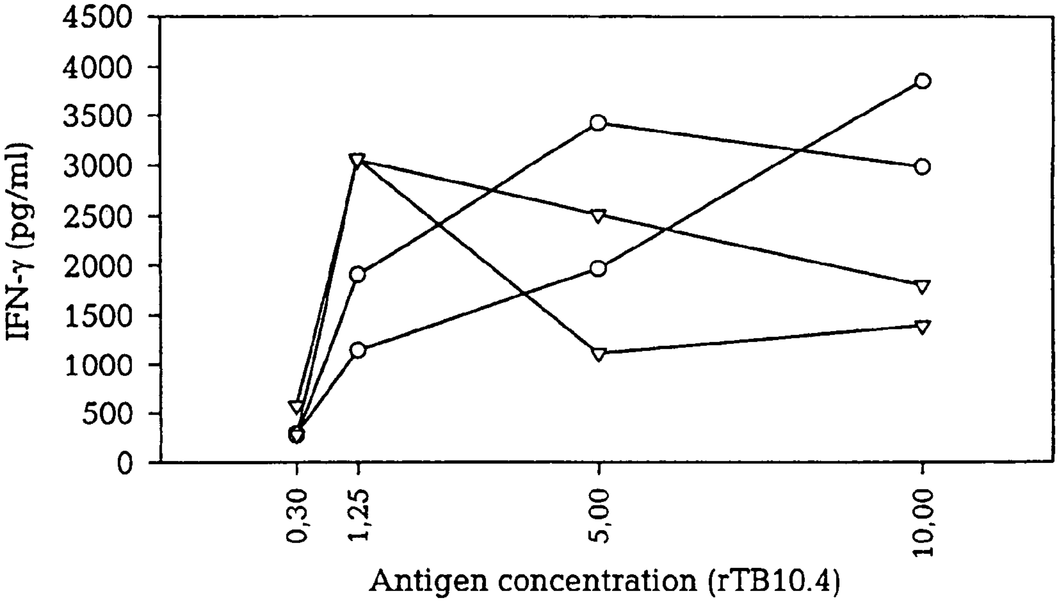
Figure 1:
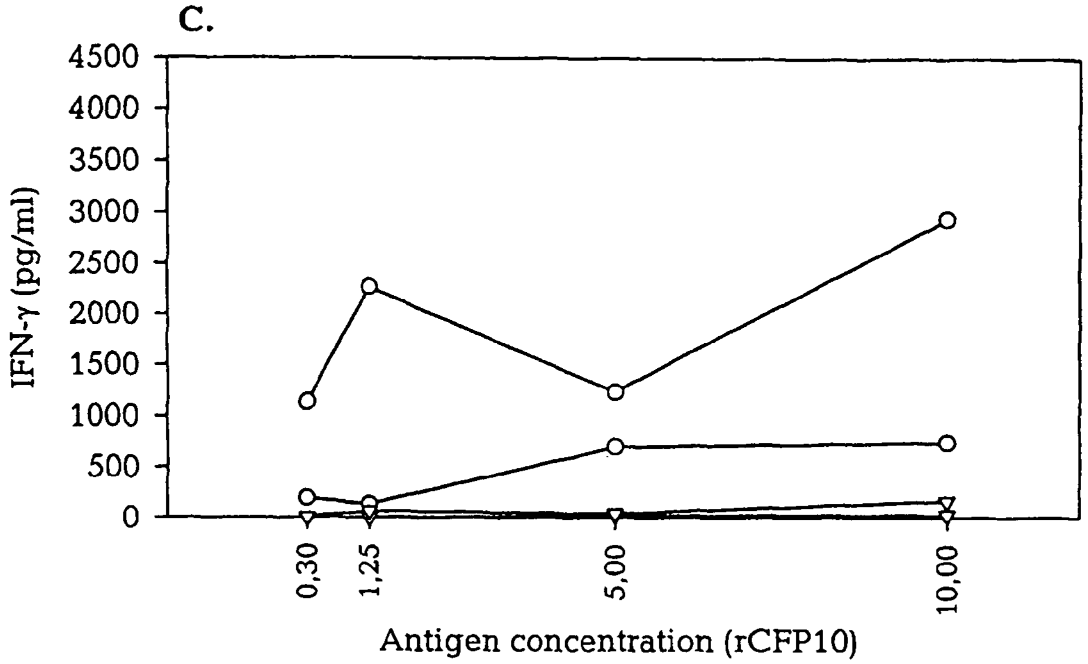

Human lymphocyte responses to rTB7.3, rTB10.4 and rCFP10. The IFN-γ response resulting from stimulation of PBMC's from two human TB patients (circles) and two healthy BCG vaccinated human donors (triangles) with increasing concentrations of rTB7.3 (FIG. 1*a*), rTB10.4 (FIG. 1*b*) and rCFP10 (FIG. 1*c*). All IFN-γ analyses were done in duplicates on supernatants pooled from three wells, and have been given as means. The variation on the duplicate wells was always less than 10% of the mean. IFN-γ levels below 50 pg/ml were considered negative.

FIGS. 2*a*, 2*b* and 2*c*.

IFN-gamma responses to low mass antigens from *M. tuberculosis* in different groups of donors. 7 healthy non-vaccinated donors (FIG. 2*a*), 7 healthy BCG vaccinated donors (FIG. 2*b*) and 17 TB patients (FIG. 2*c*) were stimulated with 5 μg/ml of ST-CF or recombinant antigens. Individual antigen specific responses are shown as delta values (IFN-gamma release in the antigen stimulated well minus IFN-gamma release in the unstimulated well). ST-CF: Short-term culture filtrate, rTB7.3: Recombinant form of Rv3221c, rTB10.4: Recombinant form of Rv0288, rCFP10: Recombinant form of CFP10, rESAT-6: Recombinant form of ESAT-6.

EXAMPLES

Example 1

The Effect of CFP10, ESAT-6, and TB10.4 on Stimulation of PBMC's From Human TB Patients The ESAT-6 antigen was identified in the low molecular mass fraction of culture filtrate due to a strong T cell response with high levels of IFN-γ released (Andersen et al 1995). This antigen has now in a number of studies been demonstrated to have good stimulatory antigenic properties and is recognized strongly by a high percentage of TB patients as well as different animal species infected with TB. Recently, a few other small proteins have been identified from various mycobacterial extracts and evaluated for their immunological relevance. Recently, a 10 kDa molecule (CFP10) encoded in the same operon as ESAT-6 was identified (Berthet, F. X. 1998).

Two novel low mass *M. tuberculosis* proteins have been identified: TB10.4, and TB7.3 (identical to Rv3221c and not a member of the ESAT-6 gene family). TB10.4 was identified as a novel member of the ESAT-6 family and our data demonstrate that the three members of the ESAT-6 family tested so far (TB10.4, CFP10 and ESAT-6), all are strongly recognized targets by the human immune response against *M. tuberculosis.*

Cloning of the Genes Encoding CFP10, TB7.3 and TB10.4.

The gene encoding CFP10 was cloned as described before (Berthet, F. X. 1998). TB7.3 (previously named CFP7A) was identified from ST-CF and the corresponding gene was cloned as described (WO98/44119).

The gene encoding TB10.4 (previously named CFP7) was identified by screening a λgt11 *M. tuberculosis* genome library with the Mab PV-2 and cloned as described previously (WO98/44119).

Expression and Purification of Recombinant TB7.3, TB10.4 and CFP10.

The histidine-tagged recombinant proteins (rTB7.3, rTB10.4 and rCFP10) were expressed and purified by metal affinity chromatography using a Talon column (Clonetech, Palo Alto, Calif.) in the presence of 8M urea, essentially as described by the manufacturer. Purification of the proteins to homogeneity was done by anion exchange chromatography using 1 ml Hitrap columns (Pharmacia, Uppsala, Sweden).

Protein concentrations were determined by the BCA-test (Micro BCA Protein Assay Reagent kit, Pierce, Oud-Beijerland, The Netherlands). LPS content in these preparations, measured by the Limulus Amoebocyte Lysate (LAL)-test, was always below 0.05 ng LPS/μg protein.

Immunological Recognition of Low Mass *M. tuberculosis* Proteins

PBMC were obtained from 17 Danish TB patients diagnosed and treated at the Department of Pulmonary Medicine, University Hospital of Copenhagen, Denmark and from 7 BCG vaccinated and 7 non-vaccinated healthy individuals with no known exposure to *M. tuberculosis*. Blood samples were drawn between 0 and 6 months after diagnosis of tuberculosis, and 2 months to 40 years after BCG vaccination.

Separation, culture of PBMC and measurement of IFN-γ in the supernatants was done as described previously by Ravn et al. A dose response study of the three recombinant proteins (rTB7.3, rTB10.4 and rCFP10) was carried out using 0.3 to 10 μg antigen/ml culture. Lymphocyte cultures from two Danish TB patients and two healthy Danish BCG vaccinated donors were stimulated with the three antigens. The lymphocyte response after stimulation with TB7.3 was low with IFN-γ releases generally below 1000 pg/ml (FIG. 1A). Neither IFN-γ nor proliferative responses to this antigen (data not shown), reached more than 20% of the responses seen with ST-CF. For the two other antigens high levels of IFN-γ were induced with increasing antigen concentrations (FIGS. 1B and C). Optimal concentrations of the antigens were between 1.25 to 10 μg/ml and these concentrations gave responses in the range of 1000-4000 pg IFN-γ/ml.

Figure 2:
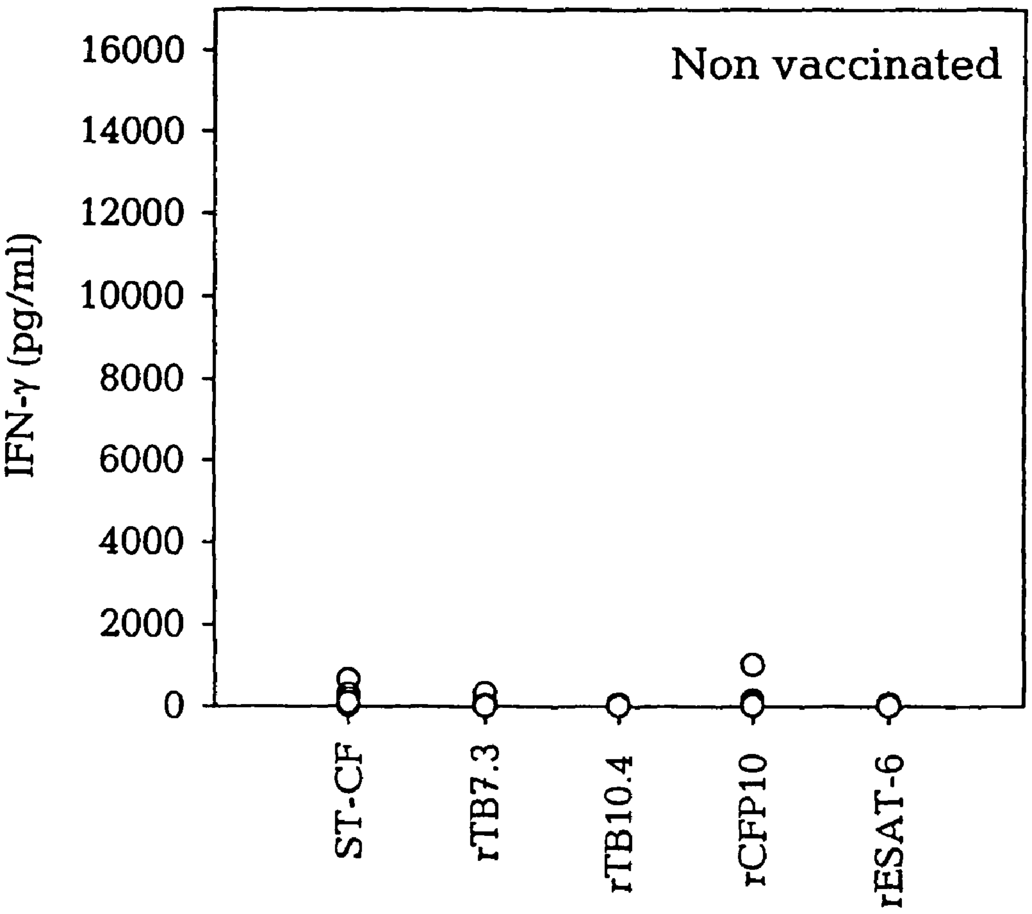
Figure 2:
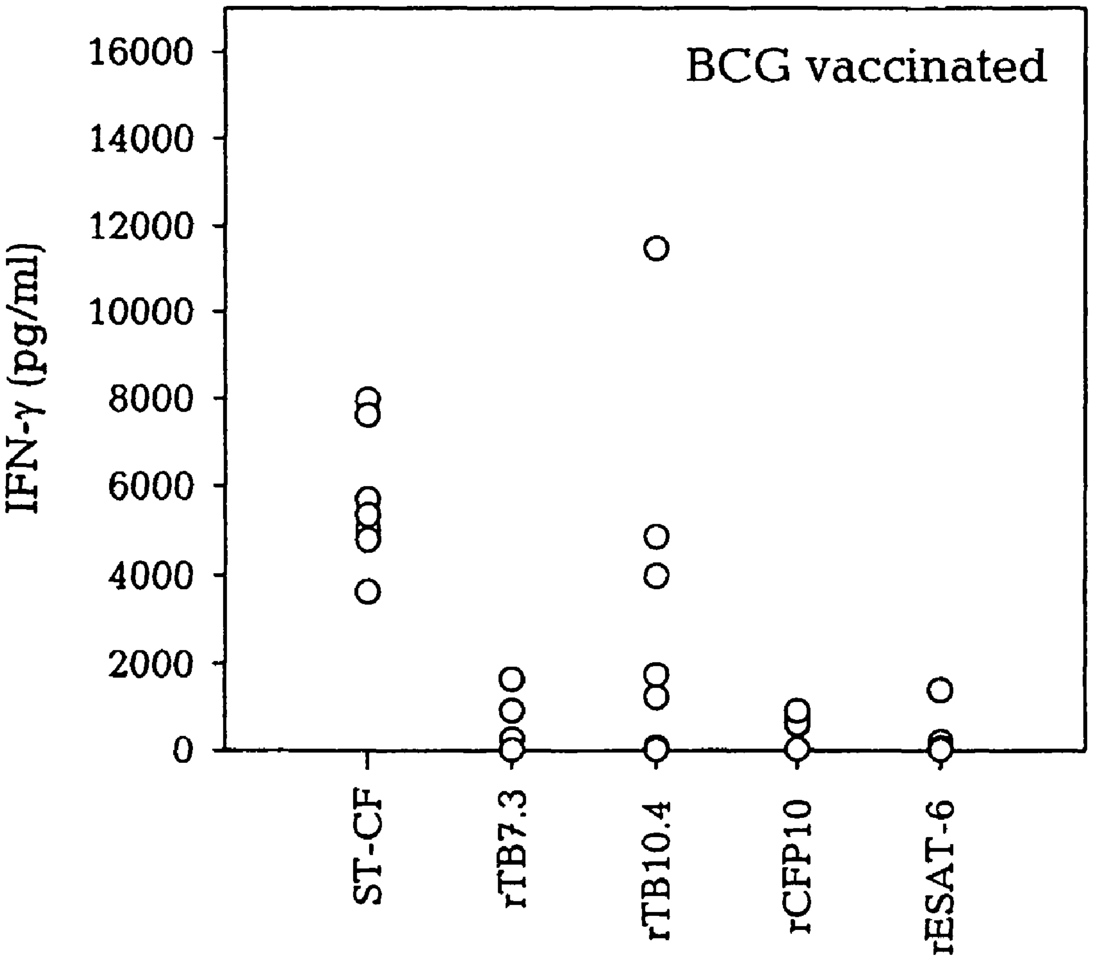
Figure 2:
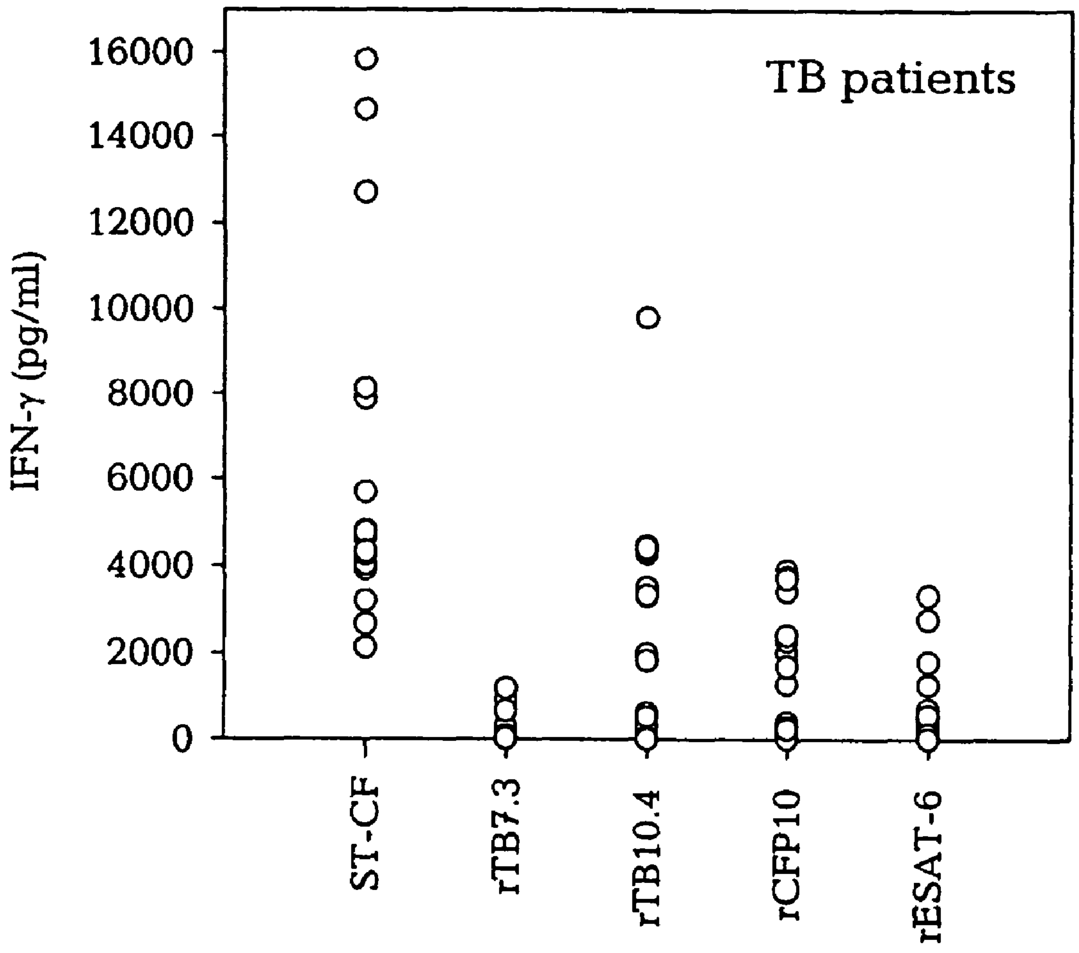

The antigens were investigated in 13-17 TB patients, 4-7 BCG vaccinated and 7 non-vaccinated donors (FIG. 2). TB7.3 was recognized but at a low level in both patients and BCG vaccinated donors. Around 40% (5 out off 13) of the TB patients recognized this molecule at a level significantly above background and for these donors the median response was 659 pg IFN-γ/ml versus 4024 pg IFN-γ/ml in the same donors for ST-CF. TB10.4 was recognized at a much higher level, by both BCG vaccinated donors (71% responders, median IFN-γ=3968 pg/ml versus 5335 pg/ml in the same donors for ST-CF), and TB patients (88% responders, median IFN-γ=3298 pg/ml versus 4707 pg/ml in the same donors for ST-CF). In the TB patients, CFP10 induced a pronounced release of IFN-γ (median IFN-γ=2135 pg/ml versus 4755 pg/ml in the same donors for ST-CF).

Compared with the pronounced T cell responses to TB10.4, CFP10 and ESAT-6, TB7.3 was a weakly recognized antigen with a very low activity.

Compared to ESAT-6, TB10.4 induced significantly higher levels of IFN-γ in TB patients (P=0.0017, Wilcoxon Signed Rank Test), whereas T cell responses to CFP10 and ESAT-6 were similar (P=0.121). Both CFP10 and TB10.4 were recognized by >70% of the TB patients, and interestingly these two potent immunogenic molecules have several points in common with ESAT-6: They have almost identical size and pl (10 kDa and 4.5) and show 15% and 21.9%, respectively, amino acid sequence identity to ESAT-6, and are members of the esat-6 gene family as previously defined.

The data presented indicate a striking focusing of the host immune response towards members of the ESAT-6 family, demonstrating that this family contains a number of molecules of potential relevance for future TB vaccines and diagnostics.

Example 2

Cloning of the Genes Encoding Low Mass Proteins from the ESAT-6 Family

The genes encoding Rv0287, Rv1036c, Rv1037c, Rv2346c, Rv2348c, Rv2653c, Rv2654c, Rv3020c, Rv3444c, Rv3445c, Rv3890c, Rv3891c, Rv3904c and Rv3905c were cloned into the expression vector pMCT3 (identical to pMCT6, Harboe et al, 1998, except that it only contains six N-terminal histidine residues), by PCR amplification with gene specific primers, for recombinant expression in *E. coli* of the proteins.

For cloning of the proteins, the following gene specific primers were used:

Rv0287:

PA0287: 5'-*CTGAGATCT*ATGAGCCTTTTGGATGC-3' (Bg/II) (SEQ ID NO: 32)

PB0287: 5'-*CTAAGCTTGGATCC*TCAGAACCCGGTATAGG-3' (BamHI) (SEQ ID NO: 33)

Rv1036c:
PA1036c: 5-CTGAGATCTTTGATCCCCGGTCGGATGGTG (Bg/II). (SEQ ID NO: 34)

PB1036c: 5'-CTCCCATGGGTCAGGTGATCGAATCAGCCA (NcoI) (SEQ ID NO: 35)

Rv1037c:
PA1037c: 5'-*CTGAGATCT*ATGACCATCAACTATC-3' (Bg/II)(SEQ ID NO: 36

PB1037c: 5'-*CTAAGCTTGGATCC*TTAGGCCCAGCTGGAGCC-3' (BamHI) (SEQ ID NO: 37)

Rv2346c:
PA2346c: 5'-CTGAGATCTATGACCATCAACTATC-3' (Bg/II) (SEQ ID NO: 38)

-continued

PB2346c: 5'-CTAAGCTTGGATCCTCAGGCCCAGCTGGAGCC-3' (BamHI) (SEQ ID NO: 39)

Rv2348c:
PA2348c: 5'-CTGAGATCTGTGCTTTTGCCTCTTGGTCCG (Bg/II)(SEQ ID NO: 40)

PB2348c: 5'-CCCAAGCTTCTAGCCGGCCGCCGGAGA (HindIII). (SEQ ID NO: 41)

Rv2653c:
PA2653c: 5'-CTGAGATCTTTGACCCACAAGCGCACTAAA (Bg/II)(SEQ ID NO: 42)

PB2653c: 5'-CTCCCATGGTCACTGTTTCGCTGTCGGGTTC (NcoI).(SEQ ID NO: 43)

Rv2654c:
PA2654c: 5'-CTGAGATCTATGAGCGGCCACGCGTTGGCT (Bg/II).(SEQ ID NO: 44)

PB2654c: 5'-CTCCCATGGTCACGGCGGATCACCCCGGTC (NcoI).(SEQ ID NO: 45)

Rv3020c:
PA3020c: 5'-CTGAGATCTATGAGTTTGTTGGATGCCCAT (Bg/II). (SEQ ID NO: 46)

PB3020c: 5'-CTCCCATGGTTAAAACCCGGTGTAGCTGGA (NcoI). (SEQ ID NO: 47)

Rv3444c:
PA3444c: 5'-*CTGAGATCT*ATGAACGCAGACCCCGTG-3' (Bg/II) (SEQ ID NO: 48)

PB3444c: 5'-*CTAAGCTTGGATCCC*TAGCGTGCCCAAGCTCC-3' (BamHI) (SEQ ID NO: 49)

Rv3445c:
PA3445c: 5'-*CTGAGATCT*ATGGTTGAACCGGGAAGG-3' (Bg/II) (SEQ ID NO: 50)

PB3445c: 5'-*CTAAGCTTGGAT*CCCTATAGGTCGCCGCCGGC-3' (BamHI) (SEQ ID NO: 51)

Rv3890c:
PA3890c: 5'-*CTGAGATCT*ATGTCAGATCAAATCACG-3' (Bg/II) (SEQ ID NO: 52)

PB3890c: 5'-*CTAAGCTTGGATCC*TTAGAACAAGCCCGCG-3' (BamHI) (SEQ ID NO: 53)

Rv3891C:
PA3891c: 5'-CTGAGATCTATGGCAGACACAATTCAGG-3' (Bg/II) (SEQ ID NO: 54)

PB3891C: 5'-CTAAGCTTCCCGGGTCAGGATCCGTGGCTAGC-3' (SmaI) (SEQ ID NO: 55)

Rv3904c:
PA3904c: 5'-*CTGAGATCT*ATGGATCCGACCGTGTTGG-3' (Bg/II) (SEQ ID NO: 56)

PB3904c: 5'-*CTGCCATGG*TCACGACCACATACCC-3' (NcoI) (SEQ ID NO: 57)

Rv3905c:
PA3905c: 5'-*CTGAGATCT*ATGGGTGCCGACGACAC-3' (Bg/II) (SEQ ID NO: 58)

PB3905c: 5'-*CTAAGCTTGGATCC*TCAGCCACCGCCCACC-3' (BamHI) (SEQ ID NO: 59)

The primers listed above create the restriction sites indicated after each sequence. The restriction sites are used for the cloning in pMCT3. Where an alternative start codon to ATG is used in the original sequence the primers introduce an ATG codon instead.

PCR reactions contained 10 ng of *M. tuberculosis* chromosomal DNA in 1×PCR buffer+Mg (Boehringer Manheim) with 400 μM dNTP mix (Boehringer Mannheim), 0.4 μM of each primer and 1.5 unit Tag DNA polymerase (Boehringer Mannheim) in 50 μA reaction volume. Reactions were initially heated to 94° C. for 5 min., run for 30 cycles of the program; 92° C. for 1 min., 52° C. for 1 min. and 72° C. for 2 min. and terminating with 72° C. for 7 min., using PTC-200 thermal cycler (M J Research, Inc.). The PCR products were cloned into the pRC2.1 cloning vector and transformed into One Shot™ *E. coli* cells (Invitrogen, Leek, The Netherlands) as described by the manufacturer. Plasmid DNA was digested with the appropriate restriction enzymes (see primer sequence) and cloned into pMCT3 and transformed into *E. coli* XL-1 Blue cells. The correct insert was always confirmed by sequencing. Sequencing of DNA was performed at Statens Serum Institute using the cycle sequencing system in combination with an automated gel reader (model 373A; Applied Biosystems).

Expression and purification of recombinant Rv0287, Rv1036c, Rv1037c, Rv2346c, Rv2348c, Rv2653c, Rv2654c, Rv3020c, Rv3444c, Rv3445c, Rv3890c, Rv3891c, Rv3904c and Rv3905c.

Expression and metal affinity purification of recombinant protein was undertaken essentially as described by the manufacturers. LB-media containing 100 μg/ml ampicillin and 12.5 μg/ml tetracyclin, was inoculated with overnight culture of XL1-Blue cells harbouring recombinant pMCT3 plasmid. The culture was shaken at 37° C. until it reached a density of $OD_{600}$=0.5. IPTG was hereafter added to a final concentration of 1 mM and the culture was further incubated 2-16 hours. Cells were harvested, resuspended in 1× sonication buffer+8 M urea and sonicated 5×30 sec. with 30 sec. pausing between the pulses. After centrifugation, the lysate was applied to a column containing 10 ml Talon resin (Clontech, Palo Alto, USA). The column was washed and eluted as described by the manufacturers.

Fractions containing recombinant protein were pooled and to gain homogenous protein preparations the pooled fractions were subjected to either the multielution technique (Andersen and Heron, 1993) or anion exchange on a Hitrap column (Pharmacia, Uppsala, Sweden).

TABLE 2

List of nucleotide sequences with their name, Open Reading Frame (ORF) and SEQ ID NOs

| Protein | ORF: | SEQ ID NO: |
|---|---|---|
| Rv0287 | 294 | 4 |
| Rv1036c | 339 | 6 |
| Rv1037c | 285 | 8 |
| Rv2346c | 282 | 10 |
| Rv2348c | 327 | 12 |
| Rv2653c | 324 | 14 |
| Rv2654c | 246 | 16 |
| Rv3020c | 294 | 18 |
| Rv3444c | 303 | 20 |
| Rv3445c | 378 | 22 |
| Rv3890c | 288 | 24 |
| Rv3891c | 324 | 26 |
| Rv3904c | 273 | 28 |
| Rv3905c | 312 | 30 |

TABLE 3

List of proteins with their name, molecular mass (measured in Daltons), their Isolectric point and their SEQ ID NO's.

| Protein | Size (aa) | Molecular Mass (Da) | Isolectric Point | SEQ ID NO: |
|---|---|---|---|---|
| CFP10 Rv3874 | 100 | 10794 | 4.41 | 1 |
| ESAT-6 Rv3875 | 95 | 9904 | 4.3 | 2 |
| TB10.4 Rv0288 | 96 | 10391 | 4.43 | 3 |
| Rv0287 | 97 | 9778.40 | 6.3111 | 5 |
| Rv1036c | 112 | 12996.06 | 4.60 | 7 |
| Rv1037c | 94 | 9833.10 | 4.543 | 9 |
| Rv2346c | 94 | 9954.01 | 4.76 | 11 |
| Rv2348c | 108 | 11396.53 | 3.89 | 13 |
| Rv2653c | 107 | 12359.82 | 8.20 | 15 |
| Rv2654c | 81 | 7697.71 | 5.04 | 17 |
| Rv3020c | 97 | 9842.03 | 6.14 | 19 |
| Rv3444c | 100 | 11120.70 | 6.165 | 21 |
| Rv3445c | 125 | 13495.10 | 6.489 | 23 |
| Rv3890c | 95 | 9920.40 | 4.176 | 25 |
| Rv3891c | 107 | 11193.70 | 4.619 | 27 |
| Rv3904c | 90 | 9602.90 | 5.480 | 29 |
| Rv3905c | 103 | 10460.30 | 4.641 | 31 |

Synthesis of Synthetic Peptides

Three of the antigens (Rv3444c, Rv3890c and Rv3905c) were synthesised as synthetic peptides by standard solid-phase methods on an ABIMED peptide synthesiser (ABIMED, Langenfeld, Germany) at Dept. of infectious diseases and Immunohematology/Bloodbank C5-P, Leiden University Medical Centre, Albinusdreef 2, 2333 Leiden, The Netherlands.

The peptides covered the following amino acids;

Rv3444c p1: SEQ. ID. NO. 21: amino acid 1-18
Rv3444c p2: SEQ. ID. NO. 21: amino acid 11-28
Rv3444c p3: SEQ. ID. NO. 21: amino acid 21-38
Rv3444c p4: SEQ. ID. NO. 21: amino acid 31-48
Rv3444c p5: SEQ. ID. NO. 21: amino acid 41-58
Rv3444c p6: SEQ. ID. NO. 21: amino acid 51-68
Rv3444c p7: SEQ. ID. NO. 21: amino acid 61-78
Rv3444c p8: SEQ. ID. NO. 21: amino acid 71-88
Rv3444c p9: SEQ. ID. NO. 21: amino acid 81-100
Rv3890c p1: SEQ. ID. NO. 25: amino acid 1-18
Rv3890c p2: SEQ. ID. NO. 25: amino acid 11-28
Rv3890c p3: SEQ. ID. NO. 25: amino acid 21-38
Rv3890c p4: SEQ. ID. NO. 25: amino acid 31-48
Rv3890c p5: SEQ. ID. NO. 25: amino acid 41-58
Rv3890c p6: SEQ. ID. NO. 25: amino acid 51-68
Rv3890c p7: SEQ. ID. NO. 25: amino acid 61-78
Rv3890c p8: SEQ. ID. NO. 25: amino acid 71-95
Rv3905c p1: SEQ. ID. NO. 31: amino acid 1-18
Rv3905c p2: SEQ. ID. NO. 31: amino acid 11-28
Rv3905c p3: SEQ. ID. NO. 31: amino acid 21-38
Rv3905c p4: SEQ. ID. NO. 31: amino acid 31-48
Rv3905c p5: SEQ. ID. NO. 31: amino acid 41-58
Rv3905c p6: SEQ. ID. NO. 31: amino acid 51-68
Rv3905c p7: SEQ. ID. NO. 31: amino acid 61-78
Rv3905c p8: SEQ. ID. NO. 31: amino acid 71-88
Rv3905c p9: SEQ. ID. NO. 31: amino acid 81-103

Example 3A

Interferon-γ Induction of T Cell Lines

The purified recombinant proteins were screened for the ability to induce a T cell response measured as IFN-γ release. The screening involved testing of the IFN-γ induction of T cell lines generated from PPD positive donors and/or a measurement of the response in PBMC preparations obtained from TB patients, PPD positive as well as negative healthy donors.

Human donors: PBMC were obtained from healthy donors with a positive in vitro response to PPD.

T cell line preparation: T cell lines were prepared by culturing 1-5×$10^6$ freshly isolated PBMC with viable *M. tuberculosis* for 1½ hour at a ratio of 5 bacteria per cell in a total volume of 1 ml (Donor 1 and 2). After washing, the cells were cultured in RPM' 1640 medium (Gibco, Grand Island, N.Y) supplemented with HEPES, and 10% heat-inactivated NHS. Alternatively, T cell lines were prepared by culturing 1-5×$10^6$ freshly isolated PBMC with 5 μg/ml of ST-CF (Donor 3-5). After 7 days in culture at 37° C. and 5% $CO_2$, T cells were supplemented with 30-50 U/well of r-IL-2 (recombinant interleukin-2) (Boehringer Mannheim) for approximately 7 days. Finally, the T cell lines were tested for reactivity against the recombinant antigens and synthetic peptides by stimulating 1-5×$10^5$ cells/ml with 5 μg/ml of PPD and/or ST-CF, recombinant Rv2653c, Rv3891c, Rv3904c and peptide pools (2-9 peptides) of Rv3444c, Rv3890c and Rv3905c, in the presence of 5×$10^5$ autologous antigen-presenting cells/ml (donor 1 and 2) or 1×$10^6$ cells/ml of irradiated (2000 RAD) autologous PBMC (donor 3-5). No antigen (No ag) and PHA were used as negative and positive controls, respectively. The supernatants were harvested after 4 days of culture and stored at −20° C. until the presence of IFN-γ were analysed.

Responses obtained with different T cell lines are shown in Table 4, where donor 1 and 2 are based on T cell lines driven by viable *M. tuberculosis* whereas donor 3-5 are generated by stimulation with ST-CF.

The results shown in Table 4, regarding the recombinant antigens Rv2653c, Rv3891c and Rv3904c and the peptides covering the antigens Rv3444c, Rv3890c and Rv3905c, indicate that these antigens can induce IFN-γ production in T-cell lines generated from PPD positive individuals.

Example 3B

Interferon-γ Induction in Human TB Patients and BCG Vaccinated

Human donors: PBMC were obtained from healthy BCG vaccinated donors with no known exposure to *M. tuberculosis* and from patients with culture or microscopy proven infection with TB. Blood samples were drawn from the TB patients 0-6 months after diagnosis.

Lymphocyte preparations and cell culture: PBMC were freshly isolated by gradient centrifugation of heparinized blood on Lymphoprep (Nycomed, Oslo, Norway) and stored in liquid nitrogen until use. The cells were resuspended in complete RPMI 1640 medium (Gibco, Grand Island, N.Y.) supplemented with 1% penicillin/streptomycin (Gibo BRL, Life Technologies), 1% non-essential-amino acids (FLOW, ICN Biomedicals, CA, USA), and 10% normal human AB0 serum (NHS) from the local blood bank. The number and the viability of the cells were determined by Nigrosin staining. Cultures were established with 1.25×$10^5$ PBMCs in 50 μl in microtitre plates (Nunc, Roskilde, Denmark) and stimulated with ST-CF PDD, Rv0287, Rv1036c, Rv1037c, Rv2653c, Rv3445c, Rv3891c, and Rv3904c. No antigen (No ag) and phytohaemagglutinin (PHA) were used as negative and positive control, respectively. Supernatants for the detection of cytokines were harvested after 5 days of culture, pooled, and stored at −80° C. until used.

Cytokine analysis: Interferon-γ (IFN-γ) was detected with a standard sandwich ELISA technique using a commercially

TABLE 4

Stimulation of T cell lines with recombinant antigen and pools of synthetic peptides. Responses to PHA and PPD or ST-CF are shown for comparison. Results are presented as pg IFN-γ/ml.

| Donor | No ag | PHA (1 μg/ml) | PPD (5 μg/ml) | Rv2653c (5 μg/ml, 1 μg/ml) | Rv3444c p1-4 (5 μg/ml, 1 μg/ml) | Rv3444c p5-9 (5 μg/ml, 1 μg/ml) |
|---|---|---|---|---|---|---|
| 1 | 350 | 3940 | 3690 | 1283, 853 | 132, 602 | 330, 553 |
| 2 | 325 | 3845 | 1824 | 673, 270 | 454, 558 | 1578, 1570 |

| Donor | Rv3890c p1-4 (5 μg/ml, 1 μg/ml) | Rv3890c p5-9 (5 μg/ml, 1 μg/ml) | Rv3904c (5 μg/ml, 1 μg/ml) | Rv3905c p1-4 (5 μg/ml, 1 μg/ml) | Rv3905c p5-9 (5 μg/ml, 1 μg/ml) |
|---|---|---|---|---|---|
| 1 | 1167, 872 | 915, 1109 | 1827, 1146 | 1250, 622 | 332, 778 |
| 2 | 318, 362 | 522, 242 | 296, 664 | 503, 874 | 817, 422 |

| Donor | No ag | PHA (1 μg/ml) | ST-CF (5 μg/ml) | Rv3891c (5 μg/ml, 0.5 μg/ml) | Rv3444c p1 + 3 (5 μg/ml, 0.5 μg/ml) | Rv3444c p2 (5 μg/ml, 0.5 μg/ml) |
|---|---|---|---|---|---|---|
| 3 | 136 | 4467 | 2425 | 1260, 606 | 223, 166 | 58, 154 |
| 4 | 0 | 5410 | 4490 | 23, 5 | 14, 12 | 12, 32 |
| 5 | 0 | 1996 | 1175 | 472, 479 | 254, 20 | 26, 33 |

| Donor | Rv3444c p4 (5 μg/ml, 0.5 μg/ml) | Rv3444c p5-6 (5 μg/ml, 0.5 μg/ml) | Rv3444c p7-9 (5 μg/ml, 0.5 μg/ml) | Rv3444c p1-9 (5 μg/ml, 0.5 μg/ml) | Rv3905c p1-9 (5 μg/ml, 0.5 μg/ml) |
|---|---|---|---|---|---|
| 3 | 59, 93 | 700, 682 | 596, 298 | 308, 225 | 262, 116 |
| 4 | 33, 34 | 109, 69 | 240, 87 | 43, 17 | 452, 25 |
| 5 | 19, 16 | 119, 148 | 162, 29 | 319, 16 | 407, 26 |

available pair of monoclonal antibodies (Endogen) and used according to the manufacturer's instruction. Recombinant IFN-γ (Endogen) was used as a standard. All data are means of duplicate wells and the variation between wells did not exceed 10% of the mean. Cytokine levels below 50 pg/ml were considered negative. Responses of 42 individual donors are shown in Table 5 and Table 6.

As shown in Table 5, marked release of IFN-γ is observed after stimulation with several of the recombinant proteins. For 6 donors, stimulation with Rv0287 give rise to high IFN-γ responses. Between 40% and 60% of the donors show intermediate IFN-γ responses when stimulated with Rv1037c, Rv3891c and Rv3904c, whereas only limited responses are obtained by stimulation with Rv3445c in this experiment.

TABLE 5

Stimulation of PBMCs from 4 healthy non-BCG vaccinated, 4 healthy BCG vaccinated and 6 TB patients with recombinant antigen. Responses to ST-CF and PHA are shown for comparison. Results are given as pg IFN-γ/ml.

| Donor | No ag | PHA (1 μg/ml) | ST-CF (5 μg/ml) | Rv0287 (10 μg/ml) | Rv1037c (10 μg/ml) | Rv3445c (10 μg/ml) | Rv3891c (10 μg/ml) | Rv3904c (10 μg/ml) |
|---|---|---|---|---|---|---|---|---|
| BCG vaccinated control donors, no known TB exposure | | | | | | | | |
| 1 | 0 | 8305 | 622 | 1459 | 1800 | 5 | 2159 | 27 |
| 2 | 82 | 20862 | 15759 | 32 | 30 | 35 | 461 | 50 |
| 3 | 7 | 17785 | 16198 | 380 | 53 | 79 | 610 | 76 |
| 4 | 912 | 16198 | 11350 | 3020 | 3137 | 799 | 8137 | 716 |
| TB patients | | | | | | | | |
| 1 | 60 | 12301 | 11057 | 2225 | 799 | 338 | 2115 | 94 |
| 2 | 7 | 10390 | 6123 | 51 | 44 | 20 | 0 | 522 |
| 3 | 34 | 11678 | 8136 | 1437 | 665 | 84 | 0 | 528 |
| 4 | 0 | 13459 | 7731 | 17 | 0 | 0 | 0 | 0 |
| 5 | 21 | 10143 | 9513 | 7869 | 3135 | 1646 | 4116 | 3018 |
| 6 | 0 | 10795 | 10932 | 8610 | 1409 | 421 | 9 | 1080 |
| Non-vaccinated control donors, no known TB exposure | | | | | | | | |
| 1 | 61 | 8379 | 511 | 23 | 115 | 0 | 604 | 269 |
| 2 | 16 | 11005 | 1923 | 12 | 23 | 8 | 615 | 16 |
| 3 | 0 | 10190 | 126 | 0 | 0 | 0 | 249 | 0 |
| 4 | 51 | 10819 | 1030 | 0 | 0 | 0 | n.d. | 0 |

TABLE 6

Stimulation of PBMCs from 9 healthy PPD and/or ST-CF negative, 13 healthy PPD and/or ST-CF positive donors and 6 Tb patients with recombinant antigen. ST-CF, PPD and PHA are shown for comparison.
Results are given in pg IFN-γ/ml.

Healthy PPD and/or ST-CF negative donors.

| Donor | no ag | PHA | PPD | STCF (2.5 μg/ml) | Rv1036c (10 μg/ml) | Rv1036c (5 μg/ml) | Rv1036c (2.5 μg/ml) | Rv2653c (5 μg/ml) | Rv2653c (2.5 μg/ml) | Rv3891c (10 μg/ml) | Rv3891c (2.5 μg/ml) | Rv3904c (10 μg/ml) | Rv3904c (2.5 μg/ml) |
|---|---|---|---|---|---|---|---|---|---|---|---|---|---|
| A | 0 | 3354 | 113 | nd. | n.d. | 0 | 37 | 0 | 4 | n.d. | n.d. | nd. | nd. |
| B | 0 | 3803 | 563 | nd. | nd. | 15 | 14 | 0 | 50 | n.d. | n.d. | nd. | nd. |
| C | 0 | 3446 | 525 | nd. | nd. | 138 | 59 | 97 | 0 | nd. | nd. | nd. | nd. |
| D | 32 | 1919 | nd. | 234 | 137 | n.d. | 148 | nd. | nd. | nd. | nd. | nd. | nd. |
| E | 0 | 2889 | nd. | 178 | 59 | n.d. | 206 | nd. | nd. | nd. | nd. | nd. | nd. |
| F | 42 | 3998 | nd. | 175 | 15 | nd. | 67 | nd. | nd. | nd. | nd. | nd. | nd. |
| G | 44 | 6269 | 190 | 195 (5 μg) | 340 | nd. | 173 | nd. | nd. | 30 | 51 | 22 | 41 |
| H | 5 | 2282 | n.d. | 10 (5 μg) | 3 | nd. | 2 | nd. | nd. | 27 | 16 | nd. | nd. |
| I | 2 | 10427 | n.d. | 80 (5 μg) | 7 | nd. | 5 | nd. | nd. | 412 | 300 | nd. | nd. |

Healthy PPD and/or ST-CF positive donors.

| Donor | no ag | PHA | PPD | STCF (5 μg/ml) | Rv1036c (10 μg/ml) | Rv1036c (5 μg/ml) | Rv1036c (2.5 μg/ml) | Rv2653c (5 μg/ml) | Rv2653c (2.5 μg/ml) | Rv3891c (10 μg/ml) | Rv3891c (2.5 μg/ml) | Rv3904c (10 μg/ml) | Rv3904c (2.5 μg/ml) |
|---|---|---|---|---|---|---|---|---|---|---|---|---|---|
| A | 31 | 6716 | 2275 | nd. | nd. | 687 | 900 | 1 | 62 | nd. | nd. | nd. | nd. |
| B | 43 | 4733 | 6159 | nd. | nd. | 2244 | 1108 | 179 | 126 | nd. | nd. | nd. | nd. |
| C | 7 | 6165 | 5808 | nd. | nd. | 4074 | 3788 | 110 | 30 | nd. | nd. | nd. | nd. |
| D | 63 | 6532 | 6314 | nd. | nd. | 1589 | 1450 | 2445 | 235 | nd. | nd. | nd. | nd. |
| E | 14 | 5614 | 3852 | nd. | nd. | 390 | 738 | 147 | 448 | nd. | nd. | nd. | nd. |
| F | 13 | 3493 | 4327 | 3381 | 229 | nd. | 605 | nd. | nd. | 8 | 25 | 42 | 61 |
| G | 12 | 8164 | nd. | 738 | 1774 | nd. | 2771 | nd. | nd. | 30 | 76 | 25 | 96 |
| H | 5 | 7378 | 840 | nd. | 568 | nd. | 948 | nd. | nd. | 15 | 19 | 730 | 102 |
| I | 0 | 5168 | n.d. | 4241 | nd. | 0 | 0 | nd. | nd. | 575 | 447 | nd. | nd. |
| J | 12 | 4873 | nd. | 745 | nd. | 4 | 3 | nd. | nd. | 511 | 214 | nd. | nd. |
| K | 1 | 4512 | nd. | 2137 | nd. | 5 | 1 | nd. | nd. | 1903 | 1105 | nd. | nd. |
| L | 75 | 8047 | nd. | 2778 | 812 | nd. | 235 | nd. | nd. | nd. | nd. | nd. | nd. |
| M | 52 | 6095 | nd. | 9133 | 1368 | nd. | 1223 | nd. | nd. | nd. | nd. | nd. | nd. |

Tb patients

| Donor | no ag | PHA | PPD | STCF (5 μg/ml) | Rv1036c (10 μg/ml) | Rv1036c (2.5 μg/ml) | Rv3904c (10 μg/ml) | Rv3904c (2.5 μg/ml) |
|---|---|---|---|---|---|---|---|---|
| A | 5 | 5282 | 4647 | nd. | 844 (5 μg/ml) | 557 | nd. | nd. |
| B | 60 | 7239 | nd. | 5474 | 301 | 595 | nd. | nd. |
| C | 44 | 11014 | nd. | 11639 | 384 | 646 | nd. | nd. |
| 0 | 8 | 5757 | 1095 | 877 | 624 | 692 | 31 | 88 |
| E | 25 | 7135 | 7118 | 5881 | 362 | 1035 | 55 | 54 |
| F | 23 | 6415 | 6085 | 6123 | 145 | 237 | 985 | 657 |

The results shown in Table 6 regarding the recombinant antigens Rv1036c, Rv2653c, Rv3891c and Rv3904c indicate that these antigens can induce IFN-γ production in PBMCs from healthy PPD and/or ST-CF positive individuals and/or Tb patients.

The invention claimed is:

1. A substantially pure polypeptide selected from the group consisting of a short peptide of at least seven consecutive amino acids and at most 10 consecutive amino acids, an oligopeptide of at least 11 consecutive amino acids and at most 100 consecutive amino acids and a longer polypeptide of at least 101 consecutive amino acids and at most 150 consecutive amino acids, wherein said substantially pure polypeptide comprises a) an amino acid sequence encoded by a member of the esat-6 gene family, b) or comprises an amino acid analogue having a sequence identity with a polypeptide encoded by a member of the esat-6 gene family of at least 94%, wherein b) is immunologically equivalent to the polypeptide encoded by a member of the esat-6 gene family, with the proviso that the substantially pure polypeptide is not selected from the group consisting of Rv0287, Rv0288, Rv1037c, Rv1038c, Rv1197, Rv1198, Rv1792, Rv1793, Rv2346c, Rv2347c, Rv3019c, Rv3619c, Rv3620c, Rv3874, and Rv3875.

2. A substantially pure polypeptide selected from the group consisting of a short peptide of at least seven consecutive amino acids and at most 10 consecutive amino acids, an oligopeptide of at least 11 consecutive amino acids and at most 100 consecutive amino acids and a longer polypeptide of at least 101 consecutive amino acids and at most 150 consecutive amino acids, wherein said substantially pure polypeptide comprises a) the amino acid sequence set forth in SEQ ID NOs: 7, 13, 15, 17, 19, 21, 23, 25, 27, 29 or 31 or comprises, b) an amino acid sequence analogue having a sequence identity with a polypeptide selected from the group consisting of SEQ ID NOs: 7, 13, 15, 17, 19, 21, 23, 25, 27, 29 and 31 of at least 70%, wherein b) is immunologically equivalent to the polypeptide selected from the group consisting of SEQ ID NOs: 7, 13, 15, 17, 19, 21, 23, 25, 27, 29 and 31.

3. A substantially pure polypeptide selected from the group consisting of a short peptide of at least seven consecutive amino acids and at most 10 consecutive amino acids, an oligopeptide of at least 11 consecutive amino acids and at most 100 consecutive amino acids and a longer polypeptide of at least 101 consecutive amino acids and at most 150 amino acids, wherein said substantially pure polypeptide comprises a) a T-cell epitope of the amino acid sequence set forth in SEQ ID NOs: 7, 13, 15, 17, 19, 21, 23, 25, 27, 29 or 31, b) or has a sequence identity of at least 70% with a T-cell epitope of the amino acid sequence set forth in a) and is immunologically equivalent to said polypeptide.

4. The polypeptide according to any one of the preceding claims in essentially pure form.

5. The polypeptide according to claim 1, which has a length of at least 7 consecutive amino acid residues, such as at least 8, at least 9, at least 10, at least 12, at least 14, at least 16, at least 18, at least 20, at least 22, at least 24, and at least 30 consecutive amino acid residues.

6. The polypeptide according to claim 1 which is free from any signal sequence.

7. A polypeptide according to claim 1, wherein said sequence identity is at least 95%.

8. A fusion polypeptide comprising at least one polypeptide according to claim 1 and at least one fusion partner.

9. A fusion polypeptide comprising at least one fusion partner and at least one substantially pure polypeptide, wherein said substantially pure polypeptide is selected from the group consisting of a short peptide of at least seven consecutive amino acids and at most 10 consecutive amino acids, an oligopeptide of at least 11 consecutive amino acids and at most 100 consecutive amino acids and a longer polypeptide of at least 101 consecutive amino acids and at most 150 consecutive amino acids, wherein said substantially pure polypeptide comprises a) an amino acid sequence encoded by a member of the esat-6 gene family, b) or comprises an amino acid analogue having a sequence identity with a polypeptide encoded by a member of the esat-6 gene family of at least 94%, wherein b) is immunologically equivalent to the polypeptide encoded by a member of the esat-6 gene family, with the proviso that the substantially pure polypeptide is not selected from the group consisting of Rv0287, Rv0288, Rv1037c, Rv1038c, Rv1197, Rv1198, Rv1792, Rv1793, Rv2346c, Rv2347c, Rv3019c, Rv3619c, Rv3620c, Rv3874, and Rv3875, and, wherein the fusion partner is selected from the group consisting of a polypeptide as defined in any one of claims 1-3 and 5-7, and another polypeptide from a bacterium belonging to the tuberculosis complex, such as ESAT-6 or at least one T-cell epitope thereof, TB10.4 or at least one T-cell epitope thereof, and MPT59 or at least one T-cell epitope thereof.

10. A fusion polypeptide according to claim 8, wherein the fusion partner is selected from the group consisting of DnaK, GroEL, urease, glutamine synthetase, L-alanine dehydrogenase, phosphate binding protein, Ag 85 complex, HBHA (heparin binding hemagglutinin), MPT51, superoxide dismutase, α-crystallin, GroES, and MPT59.

11. A polypeptide according to claim 1 which is lipidated so as to allow a self-adjuvating effect of the polypeptide.

12. An immunologic composition comprising at least one polypeptide according to claim 1.

13. An immunologic composition according to claim 12, which further comprises an immunologically and pharmaceutically acceptable carrier, vehicle or adjuvant.

14. An immunologic composition according to claim 13, wherein the carrier is selected from the group consisting of a polymer to which the polypeptide(s) is/are bound by hydrophobic non-covalent interaction, such as a plastic, e.g. polystyrene, a polymer to which the polypeptide(s) is/are covalently bound, such as a polysaccharide, and a polypeptide, e.g. bovine serum albumin, ovalbumin or keyhole limpet hemocyanin; the vehicle is selected from the group consisting of a diluent and a suspending agent; and the adjuvant is selected from the group consisting of dimethyldioctadecylammonium bromide (DDA), Quil A, poly I:C, Freund's incomplete adjuvant, IFN-γ, IL-2, IL-12, monophosphoryl lipid A (MPL), and muramyl dipeptide (MDP).

15. An immunologic composition according to any one of claims 12-14, comprising at least two of said polypeptides.

16. An immunologic composition according to claim 15, comprising 3-20 of said polypeptides.

17. A composition for diagnosing tuberculosis in an animal, including a human being, comprising a polypeptide according to claims 1.

18. A polypeptide according to claim 1, wherein said sequence identity is at least 96%.

19. A polypeptide according to claim 1, wherein said sequence identity is at least 97%.

20. A polypeptide according to claim 1, wherein said sequence identity is at least 98%.

21. A polypeptide according to claim 1, wherein said sequence identity is at least 99%.

22. A polypeptide according to claim 1, wherein said sequence identity is 100%.

* * * * *

SEQUENCE LISTING

```
<160> NUMBER OF SEQ ID NOS: 59

<210> SEQ ID NO 1
<211> LENGTH: 100
<212> TYPE: PRT
<213> ORGANISM: M. tuberculosis

<400> SEQUENCE: 1

Met Ala Glu Met Lys Thr Asp Ala Ala Thr Leu Ala Gln Glu Ala Gly
 1               5                  10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 2
<211> LENGTH: 95
<212> TYPE: PRT
<213> ORGANISM: M. tuberculosis

<400> SEQUENCE: 2

Met Thr Glu Gln Gln Trp Asn Phe Ala Gly Ile Glu Ala Ala Ala Ser
 1               5                  10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 3
<211> LENGTH: 96
<212> TYPE: PRT
<213> ORGANISM: M. tuberculosis

<400> SEQUENCE: 3

Met Ser Gln Ile Met Tyr Asn Tyr Pro Ala Met Leu Gly His Ala Gly
 1               5                  10                  15

Asp Met Ala Gly Tyr Ala Gly Thr Leu Gln Ser Leu Gly Ala Glu Ile
            20                  25                  30
```

-continued

```
Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95


<210> SEQ ID NO 4
<211> LENGTH: 294
<212> TYPE: DNA
<213> ORGANISM: M. tuberculosis
<220> FEATURE:
<221> NAME/KEY: CDS
<222> LOCATION: (1)...(294)

<400> SEQUENCE: 4

atg agc ctt ttg gat gct cat atc cca cag ttg gtg gcc tcc cag tcg       48
Met Ser Leu Leu Asp Ala His Ile Pro Gln Leu Val Ala Ser Gln Ser
1               5                   10                  15

gcg ttt gcc gcc aag gcg ggg ctg atg cgg cac acg atc ggt cag gcc       96
Ala Phe Ala Ala Lys Ala Gly Leu Met Arg His Thr Ile Gly Gln Ala
            20                  25                  30

gag cag gcg gcg atg tcg gct cag gcg ttt cac cag ggg gag tcg tcg      144
Glu Gln Ala Ala Met Ser Ala Gln Ala Phe His Gln Gly Glu Ser Ser
        35                  40                  45

gcg gcg ttt cag gcc gcc cat gcc cgg ttt gtg gcg gcg gcc gcc aaa      192
Ala Ala Phe Gln Ala Ala His Ala Arg Phe Val Ala Ala Ala Ala Lys
    50                  55                  60

gtc aac acc ttg ttg gat gtc gcg cag gcg aat ctg ggt gag gcc gcc      240
Val Asn Thr Leu Leu Asp Val Ala Gln Ala Asn Leu Gly Glu Ala Ala
65                  70                  75                  80

ggt acc tat gtg gcc gcc gat gct gcg gcc gcg tcg acc tat acc ggg      288
Gly Thr Tyr Val Ala Ala Asp Ala Ala Ala Ala Ser Thr Tyr Thr Gly
                85                  90                  95

ttc tga                                                              294
Phe


<210> SEQ ID NO 5
<211> LENGTH: 97
<212> TYPE: PRT
<213> ORGANISM: M. tuberculosis

<400> SEQUENCE: 5

Met Ser Leu Leu Asp Ala His Ile Pro Gln Leu Val Ala Ser Gln Ser
 1               5                  10                  15

Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
        35                  40                  45

Ala Ala Phe Gln Ala Ala His Ala Arg Phe Val Ala Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ala Ser Thr Tyr Thr Gly
                85                  90                  95

Phe
```

-continued

<210> SEQ ID NO 6
<211> LENGTH: 339
<212> TYPE: DNA
<213> ORGANISM: M. tuberculosis
<220> FEATURE:
<221> NAME/KEY: CDS
<222> LOCATION: (1)...(339)

<400> SEQUENCE: 6

```
ttg atc ccc ggt cgg atg gtg ctg aac tgg gaa gat ggc ctc aat gcc       48
Leu Ile Pro Gly Arg Met Val Leu Asn Trp Glu Asp Gly Leu Asn Ala
1               5                   10                  15

ctt gtt gcg gaa ggg att gag gcc atc gtg ttt cgt act tta ggc gat       96
Leu Val Ala Glu Gly Ile Glu Ala Ile Val Phe Arg Thr Leu Gly Asp
            20                  25                  30

cag tgc tgg ttg tgg gag tcg ctg ctg ccc gac gag gtg cgc cga ctg      144
Gln Cys Trp Leu Trp Glu Ser Leu Leu Pro Asp Glu Val Arg Arg Leu
        35                  40                  45

ccc gag gaa ctg gcc cgg gtg gac gca ttg ttg gac gat ccg gcg ttc      192
Pro Glu Glu Leu Ala Arg Val Asp Ala Leu Leu Asp Asp Pro Ala Phe
    50                  55                  60

ttc gcc ccg ttc gtg ccg ttc ttc gac ccg cgc agg ggc cgg ccg tcg      240
Phe Ala Pro Phe Val Pro Phe Phe Asp Pro Arg Arg Gly Arg Pro Ser
65                  70                  75                  80

acg ccg atg gag gtc tat ctg cag ttg atg ttt gtg aag ttc cgc tac      288
Thr Pro Met Glu Val Tyr Leu Gln Leu Met Phe Val Lys Phe Arg Tyr
                85                  90                  95

cgg ctg ggc tat gag tcg ctg tgc cgg gag gtg gct gat tcg atc acc      336
Arg Leu Gly Tyr Glu Ser Leu Cys Arg Glu Val Ala Asp Ser Ile Thr
            100                 105                 110

tga                                                                  339
```

<210> SEQ ID NO 7
<211> LENGTH: 112
<212> TYPE: PRT
<213> ORGANISM: M. tuberculosis

<400> SEQUENCE: 7

```
Met Ile Pro Gly Arg Met Val Leu Asn Trp Glu Asp Gly Leu Asn Ala
 1               5                  10                  15

Leu Val Ala Glu Gly Ile Glu Ala Ile Val Phe Arg Thr Leu Gly Asp
            20                  25                  30

Gln Cys Trp Leu Trp Glu Ser Leu Leu Pro Asp Glu Val Arg Arg Leu
        35                  40                  45

Pro Glu Glu Leu Ala Arg Val Asp Ala Leu Leu Asp Asp Pro Ala Phe
    50                  55                  60

Phe Ala Pro Phe Val Pro Phe Phe Asp Pro Arg Arg Gly Arg Pro Ser
65                  70                  75                  80

Thr Pro Met Glu Val Tyr Leu Gln Leu Met Phe Val Lys Phe Arg Tyr
                85                  90                  95

Arg Leu Gly Tyr Glu Ser Leu Cys Arg Glu Val Ala Asp Ser Ile Thr
            100                 105                 110
```

<210> SEQ ID NO 8
<211> LENGTH: 285
<212> TYPE: DNA
<213> ORGANISM: M. tuberculosis
<220> FEATURE:
<221> NAME/KEY: CDS
<222> LOCATION: (1)...(285)

-continued

<400> SEQUENCE: 8

```
atg acc atc aac tat caa ttc ggg gac gtc gac gct cac ggc gcc atg       48
Met Thr Ile Asn Tyr Gln Phe Gly Asp Val Asp Ala His Gly Ala Met
1               5                   10                  15

atc cgc gct cag gcc ggg tcg ctg gag gcc gag cat cag gcc atc att       96
Ile Arg Ala Gln Ala Gly Ser Leu Glu Ala Glu His Gln Ala Ile Ile
            20                  25                  30

tct gat gtg ttg acc gcg agt gac ttt tgg ggc ggc gcc ggt tcg gcg      144
Ser Asp Val Leu Thr Ala Ser Asp Phe Trp Gly Gly Ala Gly Ser Ala
        35                  40                  45

gcc tgc cag ggg ttc att acc cag ctg ggc cgt aac ttc cag gtg atc      192
Ala Cys Gln Gly Phe Ile Thr Gln Leu Gly Arg Asn Phe Gln Val Ile
    50                  55                  60

tac gag cag gcc aac gcc cac ggg cag aag gtg cag gct gcc ggc aac      240
Tyr Glu Gln Ala Asn Ala His Gly Gln Lys Val Gln Ala Ala Gly Asn
65                  70                  75                  80

aac atg gca caa acc gac agc gcc gtc ggc tcc agc tgg gcc taa          285
Asn Met Ala Gln Thr Asp Ser Ala Val Gly Ser Ser Trp Ala
                85                  90
```

<210> SEQ ID NO 9
<211> LENGTH: 94
<212> TYPE: PRT
<213> ORGANISM: M. tuberculosis

<400> SEQUENCE: 9

```
Met Thr Ile Asn Tyr Gln Phe Gly Asp Val Asp Ala His Gly Ala Met
 1               5                  10                  15

Ile Arg Ala Gln Ala Gly Leu Leu Glu Ala Glu His Gln Ala Ile Val
            20                  25                  30

Arg Asp Val Leu Ala Ala Gly Asp Phe Trp Gly Gly Ala Gly Ser Val
        35                  40                  45

Ala Cys Gln Glu Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90
```

<210> SEQ ID NO 10
<211> LENGTH: 285
<212> TYPE: DNA
<213> ORGANISM: M. tuberculosis
<220> FEATURE:
<221> NAME/KEY: CDS
<222> LOCATION: (1)...(282)

<400> SEQUENCE: 10

```
atg acc atc aac tat cag ttc ggt gat gtc gac gct cat ggc gcc atg       48
Met Thr Ile Asn Tyr Gln Phe Gly Asp Val Asp Ala His Gly Ala Met
1               5                   10                  15

atc cgc gct cag gcc ggg ttg ctg gag gcg gag cat cag gcc atc gtt       96
Ile Arg Ala Gln Ala Gly Leu Leu Glu Ala Glu His Gln Ala Ile Val
            20                  25                  30

cgt gat gtg ttg gcc gcg ggt gac ttt tgg ggc ggc gcc ggt tcg gtg      144
Arg Asp Val Leu Ala Ala Gly Asp Phe Trp Gly Gly Ala Gly Ser Val
        35                  40                  45

gct tgc cag gag ttc att acc cag ttg ggc cgt aac ttc cag gtg atc      192
Ala Cys Gln Glu Phe Ile Thr Gln Leu Gly Arg Asn Phe Gln Val Ile
    50                  55                  60
```

-continued

```
tac gag cag gcc aac gcc cac ggg cag aag gtg cag gct gcc ggc aac      240
Tyr Glu Gln Ala Asn Ala His Gly Gln Lys Val Gln Ala Ala Gly Asn
65                  70                  75                  80

aac atg gca caa acc gac agc gcc gtc ggc tcc agc tgg gcc              282
Asn Met Ala Gln Thr Asp Ser Ala Val Gly Ser Ser Trp Ala
                85                  90

tga                                                                  285


<210> SEQ ID NO 11
<211> LENGTH: 94
<212> TYPE: PRT
<213> ORGANISM: M. tuberculosis

<400> SEQUENCE: 11

Met Thr Ile Asn Tyr Gln Phe Gly Asp Val Asp Ala His Gly Ala Met
 1               5                  10                  15

Ile Arg Ala Gln Ala Gly Leu Leu Glu Ala Glu His Gln Ala Ile Val
            20                  25                  30

Arg Asp Val Leu Ala Ala Gly Asp Phe Trp Gly Gly Ala Gly Ser Val
        35                  40                  45

Ala Cys Gln Glu Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90


<210> SEQ ID NO 12
<211> LENGTH: 327
<212> TYPE: DNA
<213> ORGANISM: M. tuberculosis
<220> FEATURE:
<221> NAME/KEY: CDS
<222> LOCATION: (1)...(327)

<400> SEQUENCE: 12

gtg ctt ttg cct ctt ggt ccg cct ttg ccg ccc gac gcg gtg gtg gcg       48
Val Leu Leu Pro Leu Gly Pro Pro Leu Pro Pro Asp Ala Val Val Ala
1               5                   10                  15

aaa cgg gct gag tcg gga atg ctc ggc ggg ttg tcg gtt ccg ctc agc       96
Lys Arg Ala Glu Ser Gly Met Leu Gly Gly Leu Ser Val Pro Leu Ser
            20                  25                  30

tgg gga gtg gct gtg cca ccc gat gat tat gac cac tgg gcg cct gcg      144
Trp Gly Val Ala Val Pro Pro Asp Asp Tyr Asp His Trp Ala Pro Ala
        35                  40                  45

ccg gag gac ggc gcc gat gtc gat gtc cag gcg gcc gaa ggg gcg gac      192
Pro Glu Asp Gly Ala Asp Val Asp Val Gln Ala Ala Glu Gly Ala Asp
    50                  55                  60

gca gag gcc gcg gcc atg gac gag tgg gat gag tgg cag gcg tgg aac      240
Ala Glu Ala Ala Ala Met Asp Glu Trp Asp Glu Trp Gln Ala Trp Asn
65                  70                  75                  80

gag tgg gtg gcg gag aac gct gaa ccc cgc ttt gag gtg cca cgg agt      288
Glu Trp Val Ala Glu Asn Ala Glu Pro Arg Phe Glu Val Pro Arg Ser
                85                  90                  95

agc agc agc gtg att ccg cat tct ccg gcg gcc ggc tag                  327
Ser Ser Ser Val Ile Pro His Ser Pro Ala Ala Gly
            100                 105


<210> SEQ ID NO 13
<211> LENGTH: 108
<212> TYPE: PRT
```

-continued

<213> ORGANISM: M. tuberculosis

<400> SEQUENCE: 13

```
Met Leu Leu Pro Leu Gly Pro Pro Leu Pro Pro Asp Ala Val Val Ala
 1               5                  10                  15

Lys Arg Ala Glu Ser Gly Met Leu Gly Gly Leu Ser Val Pro Leu Ser
            20                  25                  30

Trp Gly Val Ala Val Pro Pro Asp Asp Tyr Asp His Trp Ala Pro Ala
        35                  40                  45

Pro Glu Asp Gly Ala Asp Val Asp Val Gln Ala Ala Glu Gly Ala Asp
    50                  55                  60

Ala Glu Ala Ala Ala Met Asp Glu Trp Asp Glu Trp Gln Ala Trp Asn
65                  70                  75                  80

Glu Trp Val Ala Glu Asn Ala Glu Pro Arg Phe Glu Val Pro Arg Ser
                85                  90                  95

Ser Ser Ser Val Ile Pro His Ser Pro Ala Ala Gly
            100                 105
```

<210> SEQ ID NO 14
<211> LENGTH: 324
<212> TYPE: DNA
<213> ORGANISM: M. tuberculosis
<220> FEATURE:
<221> NAME/KEY: CDS
<222> LOCATION: (1)...(324)

<400> SEQUENCE: 14

```
ttg acc cac aag cgc act aaa cgc cag cca gcc atc gcc gca ggg ctc       48
Leu Thr His Lys Arg Thr Lys Arg Gln Pro Ala Ile Ala Ala Gly Leu
1               5                   10                  15

aac gcc ccg cgt cgg aat cgc gtt ggg cgg caa cat ggt tgg ccg gcc       96
Asn Ala Pro Arg Arg Asn Arg Val Gly Arg Gln His Gly Trp Pro Ala
            20                  25                  30

gac gtt ccg tcc gcc gag cag cgc cgc gcc caa cgg cag cgc gac ctc      144
Asp Val Pro Ser Ala Glu Gln Arg Arg Ala Gln Arg Gln Arg Asp Leu
        35                  40                  45

gag gct atc cgc cga gcg tac gcc gag atg gtg gcg aca tca cac gaa      192
Glu Ala Ile Arg Arg Ala Tyr Ala Glu Met Val Ala Thr Ser His Glu
    50                  55                  60

atc gac gac gac aca gcc gaa ctg gcg ctg ttg tcg atg cat ctc gac      240
Ile Asp Asp Asp Thr Ala Glu Leu Ala Leu Leu Ser Met His Leu Asp
65                  70                  75                  80

gat gag cag cgc cgg ctt gag gcg ggg atg aag ctc ggc tgg cat ccg      288
Asp Glu Gln Arg Arg Leu Glu Ala Gly Met Lys Leu Gly Trp His Pro
                85                  90                  95

tat cac ttc ccc gac gaa ccc gac agc aaa cag tga                      324
Tyr His Phe Pro Asp Glu Pro Asp Ser Lys Gln
            100                 105
```

<210> SEQ ID NO 15
<211> LENGTH: 107
<212> TYPE: PRT
<213> ORGANISM: M. tuberculosis

<400> SEQUENCE: 15

```
Met Thr His Lys Arg Thr Lys Arg Gln Pro Ala Ile Ala Ala Gly Leu
 1               5                  10                  15

Asn Ala Pro Arg Arg Asn Arg Val Gly Arg Gln His Gly Trp Pro Ala
            20                  25                  30

Asp Val Pro Ser Ala Glu Gln Arg Arg Ala Gln Arg Gln Arg Asp Leu
```

-continued

```
        35                  40                  45

Glu Ala Ile Arg Arg Ala Tyr Ala Glu Met Val Ala Thr Ser His Glu
    50                  55                  60

Ile Asp Asp Asp Thr Ala Glu Leu Ala Leu Leu Ser Met His Leu Asp
65                  70                  75                  80

Asp Glu Gln Arg Arg Leu Glu Ala Gly Met Lys Leu Gly Trp His Pro
                85                  90                  95

Tyr His Phe Pro Asp Glu Pro Asp Ser Lys Gln
            100                 105


<210> SEQ ID NO 16
<211> LENGTH: 246
<212> TYPE: DNA
<213> ORGANISM: M. tuberculosis
<220> FEATURE:
<221> NAME/KEY: CDS
<222> LOCATION: (1)...(246)

<400> SEQUENCE: 16

atg agc ggc cac gcg ttg gct gct cgg acg ttg ctg gcc gcc gcg gac       48
Met Ser Gly His Ala Leu Ala Ala Arg Thr Leu Leu Ala Ala Ala Asp
1               5                   10                  15

gag ctt gtc ggc ggc ccg cca gtc gag gct tcg gcc gcc gcg ctg gcc       96
Glu Leu Val Gly Gly Pro Pro Val Glu Ala Ser Ala Ala Ala Leu Ala
            20                  25                  30

ggc gac gcc gcg ggc gca tgg cgg acc gcg gcc gtc gag ctt gcg cga      144
Gly Asp Ala Ala Gly Ala Trp Arg Thr Ala Ala Val Glu Leu Ala Arg
        35                  40                  45

gcg ttg gtc cgc gct gtg gcg gag tcg cac ggc gtc gcg gcc gtt ttg      192
Ala Leu Val Arg Ala Val Ala Glu Ser His Gly Val Ala Ala Val Leu
    50                  55                  60

ttc gcc gcg acg gcc gcc gcg gcg gcg gcc gtc gac cgg ggt gat ccg      240
Phe Ala Ala Thr Ala Ala Ala Ala Ala Ala Val Asp Arg Gly Asp Pro
65                  70                  75                  80

ccg tga                                                              246
Pro


<210> SEQ ID NO 17
<211> LENGTH: 81
<212> TYPE: PRT
<213> ORGANISM: M. tuberculosis

<400> SEQUENCE: 17

Met Ser Gly His Ala Leu Ala Ala Arg Thr Leu Leu Ala Ala Ala Asp
 1               5                  10                  15

Glu Leu Val Gly Gly Pro Pro Val Glu Ala Ser Ala Ala Ala Leu Ala
            20                  25                  30

Gly Asp Ala Ala Gly Ala Trp Arg Thr Ala Ala Val Glu Leu Ala Arg
        35                  40                  45

Ala Leu Val Arg Ala Val Ala Glu Ser His Gly Val Ala Ala Val Leu
    50                  55                  60

Phe Ala Ala Thr Ala Ala Ala Ala Ala Ala Val Asp Arg Gly Asp Pro
65                  70                  75                  80

Pro


<210> SEQ ID NO 18
<211> LENGTH: 294
<212> TYPE: DNA
<213> ORGANISM: M. tuberculosis
<220> FEATURE:
```

-continued

<221> NAME/KEY: CDS
<222> LOCATION: (1)...(294)

<400> SEQUENCE: 18

```
atg agt ttg ttg gat gcc cat att ccg cag ttg atc gct tcg cat acg       48
Met Ser Leu Leu Asp Ala His Ile Pro Gln Leu Ile Ala Ser His Thr
1               5                   10                  15

gcg ttt gcc gct aag gcg ggg ttg atg cgg cat acg atc ggt cag gcc       96
Ala Phe Ala Ala Lys Ala Gly Leu Met Arg His Thr Ile Gly Gln Ala
            20                  25                  30

gag cag cag gcg atg tcg gcg cag gcg ttt cat cag gga gag tcc gcg      144
Glu Gln Gln Ala Met Ser Ala Gln Ala Phe His Gln Gly Glu Ser Ala
        35                  40                  45

gcg gcg ttt cag ggt gcg cat gcc cgg ttt gtg gcc gcg gcc gcc aag      192
Ala Ala Phe Gln Gly Ala His Ala Arg Phe Val Ala Ala Ala Ala Lys
    50                  55                  60

gtc aat acc ttg ctg gat atc gcg caa gcc aat ttg ggt gag gcc gcg      240
Val Asn Thr Leu Leu Asp Ile Ala Gln Ala Asn Leu Gly Glu Ala Ala
65                  70                  75                  80

ggc acg tat gtg gcc gcc gat gcc gcc gcc gcg tcc agc tac acc ggg      288
Gly Thr Tyr Val Ala Ala Asp Ala Ala Ala Ala Ser Ser Tyr Thr Gly
                85                  90                  95

ttt tta                                                              294
Phe Leu
```

<210> SEQ ID NO 19
<211> LENGTH: 97
<212> TYPE: PRT
<213> ORGANISM: M. tuberculosis

<400> SEQUENCE: 19

```
Met Ser Leu Leu Asp Ala His Ile Pro Gln Leu Ile Ala Ser His Thr
 1               5                  10                  15

Ala Phe Ala Ala Lys Ala Gly Leu Met Arg His Thr Ile Gly Gln Ala
            20                  25                  30

Glu Gln Gln Ala Met Ser Ala Gln Ala Phe His Gln Gly Glu Ser Ala
        35                  40                  45

Ala Ala Phe Gln Gly Ala His Ala Arg Phe Val Ala Ala Ala Ala Lys
    50                  55                  60

Val Asn Thr Leu Leu Asp Ile Ala Gln Ala Asn Leu Gly Glu Ala Ala
65                  70                  75                  80

Gly Thr Tyr Val Ala Ala Asp Ala Ala Ala Ala Ser Ser Tyr Thr Gly
                85                  90                  95

Phe
```

<210> SEQ ID NO 20
<211> LENGTH: 303
<212> TYPE: DNA
<213> ORGANISM: M. tuberculosis
<220> FEATURE:
<221> NAME/KEY: CDS
<222> LOCATION: (1)...(303)

<400> SEQUENCE: 20

```
atg aac gca gac ccc gtg ttg tcg tac aac ttt gac gcc atc gaa tac       48
Met Asn Ala Asp Pro Val Leu Ser Tyr Asn Phe Asp Ala Ile Glu Tyr
1               5                   10                  15

tcc gtt cgt cag gag atc cac acc acc gcg gcc cgt ttc aac gct gcg       96
Ser Val Arg Gln Glu Ile His Thr Thr Ala Ala Arg Phe Asn Ala Ala
            20                  25                  30
```

-continued

```
ctg caa gag ctg agg tcg cag atc gcg ccg ttg cag cag ctc tgg aca      144
Leu Gln Glu Leu Arg Ser Gln Ile Ala Pro Leu Gln Gln Leu Trp Thr
        35                  40                  45

cgg gaa gcg gcc gcc gcc tac cac gcg gag caa ctc aag tgg cac cag      192
Arg Glu Ala Ala Ala Ala Tyr His Ala Glu Gln Leu Lys Trp His Gln
    50                  55                  60

gcg gcc agc gcg ctc aac gag atc ctg atc gac ttg gga aac gcg gtt      240
Ala Ala Ser Ala Leu Asn Glu Ile Leu Ile Asp Leu Gly Asn Ala Val
65                  70                  75                  80

cgc cac ggt gcc gac gac gtg gcg cat gcc gac cgg cgg gcg gct gga      288
Arg His Gly Ala Asp Asp Val Ala His Ala Asp Arg Arg Ala Ala Gly
                85                  90                  95

gct tgg gca cgc tag                                                  303
Ala Trp Ala Arg
            100


<210> SEQ ID NO 21
<211> LENGTH: 100
<212> TYPE: PRT
<213> ORGANISM: M. tuberculosis

<400> SEQUENCE: 21

Met Asn Ala Asp Pro Val Leu Ser Tyr Asn Phe Asp Ala Ile Glu Tyr
 1               5                  10                  15

Ser Val Arg Gln Glu Ile His Thr Thr Ala Ala Arg Phe Asn Ala Ala
            20                  25                  30

Leu Gln Glu Leu Arg Ser Gln Ile Ala Pro Leu Gln Gln Leu Trp Thr
        35                  40                  45

Arg Glu Ala Ala Ala Ala Tyr His Ala Glu Gln Leu Lys Trp His Gln
    50                  55                  60

Ala Ala Ser Ala Leu Asn Glu Ile Leu Ile Asp Leu Gly Asn Ala Val
65                  70                  75                  80

Arg His Gly Ala Asp Asp Val Ala His Ala Asp Arg Arg Ala Ala Gly
                85                  90                  95

Ala Trp Ala Arg
            100


<210> SEQ ID NO 22
<211> LENGTH: 378
<212> TYPE: DNA
<213> ORGANISM: M. tuberculosis
<220> FEATURE:
<221> NAME/KEY: CDS
<222> LOCATION: (1)...(378)

<400> SEQUENCE: 22

ttg gtt gaa ccg gga agg atc gga ggg aac cag acg agg ttg gcg gcg       48
Leu Val Glu Pro Gly Arg Ile Gly Gly Asn Gln Thr Arg Leu Ala Ala
1               5                   10                  15

gtc cta ctt gat gtg agc aca ccg aac acg ctg aac gcc gac ttt gac       96
Val Leu Leu Asp Val Ser Thr Pro Asn Thr Leu Asn Ala Asp Phe Asp
            20                  25                  30

ctg atg cgt tcg gtt gcg ggt atc acg gac gcc cgc aat gag gaa atc      144
Leu Met Arg Ser Val Ala Gly Ile Thr Asp Ala Arg Asn Glu Glu Ile
        35                  40                  45

cgt gcg atg ctg cag gca ttc atc ggc cgc atg agc ggt gtg ccg ccg      192
Arg Ala Met Leu Gln Ala Phe Ile Gly Arg Met Ser Gly Val Pro Pro
    50                  55                  60

tcg gtg tgg ggt ggg ctc gcg gcc gct cgg ttc cag gat gtg gtg gat      240
Ser Val Trp Gly Gly Leu Ala Ala Ala Arg Phe Gln Asp Val Val Asp
65                  70                  75                  80
```

-continued

```
cgc tgg aac gcc gag tcg acg cgg ctc tac cac gtc ctg cac gcg atc      288
Arg Trp Asn Ala Glu Ser Thr Arg Leu Tyr His Val Leu His Ala Ile
                85                  90                  95

gcc gac acc atc cgc cac aac gag gcc gcg ctg cgg gaa gcc ggc caa      336
Ala Asp Thr Ile Arg His Asn Glu Ala Ala Leu Arg Glu Ala Gly Gln
            100                 105                 110

atc cat gcc cgc cac atc gcc gcc gcc ggc ggc gac cta tag              378
Ile His Ala Arg His Ile Ala Ala Ala Gly Gly Asp Leu
        115                 120                 125


<210> SEQ ID NO 23
<211> LENGTH: 125
<212> TYPE: PRT
<213> ORGANISM: M. tuberculosis

<400> SEQUENCE: 23

Met Val Glu Pro Gly Arg Ile Gly Gly Asn Gln Thr Arg Leu Ala Ala
 1               5                  10                  15

Val Leu Leu Asp Val Ser Thr Pro Asn Thr Leu Asn Ala Asp Phe Asp
            20                  25                  30

Leu Met Arg Ser Val Ala Gly Ile Thr Asp Ala Arg Asn Glu Glu Ile
        35                  40                  45

Arg Ala Met Leu Gln Ala Phe Ile Gly Arg Met Ser Gly Val Pro Pro
    50                  55                  60

Ser Val Trp Gly Gly Leu Ala Ala Ala Arg Phe Gln Asp Val Val Asp
65                  70                  75                  80

Arg Trp Asn Ala Glu Ser Thr Arg Leu Tyr His Val Leu His Ala Ile
                85                  90                  95

Ala Asp Thr Ile Arg His Asn Glu Ala Ala Leu Arg Glu Ala Gly Gln
            100                 105                 110

Ile His Ala Arg His Ile Ala Ala Ala Gly Gly Asp Leu
        115                 120                 125


<210> SEQ ID NO 24
<211> LENGTH: 288
<212> TYPE: DNA
<213> ORGANISM: M. tuberculosis
<220> FEATURE:
<221> NAME/KEY: CDS
<222> LOCATION: (1)...(288)

<400> SEQUENCE: 24

atg tca gat caa atc acg tat aac ccg gga gcc gta tcc gac ttc gct       48
Met Ser Asp Gln Ile Thr Tyr Asn Pro Gly Ala Val Ser Asp Phe Ala
1               5                   10                  15

tcc gac gtg ggc tcg cgc gcc ggc cag ctc cac atg att tac gaa gac       96
Ser Asp Val Gly Ser Arg Ala Gly Gln Leu His Met Ile Tyr Glu Asp
            20                  25                  30

acc gcc agc aaa aca aat gcg ctg caa gag ttt ttc gcg ggc cac ggc      144
Thr Ala Ser Lys Thr Asn Ala Leu Gln Glu Phe Phe Ala Gly His Gly
        35                  40                  45

gcg caa ggg ttt ttc gac gcc cag gcg cag atg ctg tcg ggg ctg cag      192
Ala Gln Gly Phe Phe Asp Ala Gln Ala Gln Met Leu Ser Gly Leu Gln
    50                  55                  60

ggg ctc att gag acg gtg ggt cag cat ggg act acc acc ggc cac gtg      240
Gly Leu Ile Glu Thr Val Gly Gln His Gly Thr Thr Thr Gly His Val
65                  70                  75                  80

ctg gac aac gcg atc gga acc gac cag gcc atc gcg ggc ttg ttc taa      288
Leu Asp Asn Ala Ile Gly Thr Asp Gln Ala Ile Ala Gly Leu Phe
                85                  90                  95
```

```
<210> SEQ ID NO 25
<211> LENGTH: 95
<212> TYPE: PRT
<213> ORGANISM: M. tuberculosis

<400> SEQUENCE: 25

Met Ser Asp Gln Ile Thr Tyr Asn Pro Gly Ala Val Ser Asp Phe Ala
 1               5                  10                  15

Ser Asp Val Gly Ser Arg Ala Gly Gln Leu His Met Ile Tyr Glu Asp
            20                  25                  30

Thr Ala Ser Lys Thr Asn Ala Leu Gln Glu Phe Phe Ala Gly His Gly
        35                  40                  45

Ala Gln Gly Phe Phe Asp Ala Gln Ala Gln Met Leu Ser Gly Leu Gln
    50                  55                  60

Gly Leu Ile Glu Thr Val Gly Gln His Gly Thr Thr Thr Gly His Val
65                  70                  75                  80

Leu Asp Asn Ala Ile Gly Thr Asp Gln Ala Ile Ala Gly Leu Phe
                85                  90                  95


<210> SEQ ID NO 26
<211> LENGTH: 324
<212> TYPE: DNA
<213> ORGANISM: M. tuberculosis
<220> FEATURE:
<221> NAME/KEY: CDS
<222> LOCATION: (1)...(324)

<400> SEQUENCE: 26

gtg gca gac aca att cag gta aca ccg cag atg ctg cgc agc acc gcc       48
Val Ala Asp Thr Ile Gln Val Thr Pro Gln Met Leu Arg Ser Thr Ala
1               5                   10                  15

aac gat atc cag gcg aat atg gag caa gcc atg gga atc gcc aag ggc       96
Asn Asp Ile Gln Ala Asn Met Glu Gln Ala Met Gly Ile Ala Lys Gly
            20                  25                  30

tac cta gcc aac cag gaa aac gtc atg aac ccc gcc acc tgg tct ggt      144
Tyr Leu Ala Asn Gln Glu Asn Val Met Asn Pro Ala Thr Trp Ser Gly
        35                  40                  45

acc ggc gtc gtt gct tcg cat atg aca gcc acc gag atc acc aat gaa      192
Thr Gly Val Val Ala Ser His Met Thr Ala Thr Glu Ile Thr Asn Glu
    50                  55                  60

ttg aac aag gtc ctt acc ggg ggc acg cgc ctg gcc gag ggc ctc gtg      240
Leu Asn Lys Val Leu Thr Gly Gly Thr Arg Leu Ala Glu Gly Leu Val
65                  70                  75                  80

cag gcc gca gcc ctg atg gag gga cac gag gcg gac tcg cag aca gcg      288
Gln Ala Ala Ala Leu Met Glu Gly His Glu Ala Asp Ser Gln Thr Ala
                85                  90                  95

ttt cag gcg ctg ttc ggc gct agc cac gga tcc tga                      324
Phe Gln Ala Leu Phe Gly Ala Ser His Gly Ser
            100                 105


<210> SEQ ID NO 27
<211> LENGTH: 107
<212> TYPE: PRT
<213> ORGANISM: M. tuberculosis

<400> SEQUENCE: 27

Met Ala Asp Thr Ile Gln Val Thr Pro Gln Met Leu Arg Ser Thr Ala
 1               5                  10                  15

Asn Asp Ile Gln Ala Asn Met Glu Gln Ala Met Gly Ile Ala Lys Gly
            20                  25                  30
```

-continued

```
Tyr Leu Ala Asn Gln Glu Asn Val Met Asn Pro Ala Thr Trp Ser Gly
        35                  40                  45

Thr Gly Val Val Ala Ser His Met Thr Ala Thr Glu Ile Thr Asn Glu
    50                  55                  60

Leu Asn Lys Val Leu Thr Gly Gly Thr Arg Leu Ala Glu Gly Leu Val
65                  70                  75                  80

Gln Ala Ala Ala Leu Met Glu Gly His Glu Ala Asp Ser Gln Thr Ala
                85                  90                  95

Phe Gln Ala Leu Phe Gly Ala Ser His Gly Ser
            100                 105


<210> SEQ ID NO 28
<211> LENGTH: 273
<212> TYPE: DNA
<213> ORGANISM: M. tuberculosis
<220> FEATURE:
<221> NAME/KEY: CDS
<222> LOCATION: (1)...(273)

<400> SEQUENCE: 28

gtg gat ccg acc gtg ttg gct gat gcg gtg gcg cgg atg gcc gaa ttc       48
Val Asp Pro Thr Val Leu Ala Asp Ala Val Ala Arg Met Ala Glu Phe
1               5                   10                  15

ggt cgc cac gtc gag gag ctg gtc gcc gag att gag tcc ttg gtt acc       96
Gly Arg His Val Glu Glu Leu Val Ala Glu Ile Glu Ser Leu Val Thr
            20                  25                  30

cgg ctg cat gtg acg tgg acg ggg gag ggc gcg gcg gct cat gct gag      144
Arg Leu His Val Thr Trp Thr Gly Glu Gly Ala Ala Ala His Ala Glu
        35                  40                  45

gcg caa cga cat tgg gct gcc ggt gag gcg atg atg cgc cag gcg ttg      192
Ala Gln Arg His Trp Ala Ala Gly Glu Ala Met Met Arg Gln Ala Leu
    50                  55                  60

gcc cag ctc acg gcc gcg ggg cag agc gcg cac gcc aac tac acc ggc      240
Ala Gln Leu Thr Ala Ala Gly Gln Ser Ala His Ala Asn Tyr Thr Gly
65                  70                  75                  80

gcg atg gcc acg aat ttg ggt atg tgg tcg tga                          273
Ala Met Ala Thr Asn Leu Gly Met Trp Ser
                85                  90


<210> SEQ ID NO 29
<211> LENGTH: 90
<212> TYPE: PRT
<213> ORGANISM: M. tuberculosis

<400> SEQUENCE: 29

Met Asp Pro Thr Val Leu Ala Asp Ala Val Ala Arg Met Ala Glu Phe
 1               5                  10                  15

Gly Arg His Val Glu Glu Leu Val Ala Glu Ile Glu Ser Leu Val Thr
            20                  25                  30

Arg Leu His Val Thr Trp Thr Gly Glu Gly Ala Ala Ala His Ala Glu
        35                  40                  45

Ala Gln Arg His Trp Ala Ala Gly Glu Ala Met Met Arg Gln Ala Leu
    50                  55                  60

Ala Gln Leu Thr Ala Ala Gly Gln Ser Ala His Ala Asn Tyr Thr Gly
65                  70                  75                  80

Ala Met Ala Thr Asn Leu Gly Met Trp Ser
                85                  90


<210> SEQ ID NO 30
```

-continued

```
<211> LENGTH: 312
<212> TYPE: DNA
<213> ORGANISM: M. tuberculosis
<220> FEATURE:
<221> NAME/KEY: CDS
<222> LOCATION: (1)...(312)

<400> SEQUENCE: 30

atg ggt gcc gac gac acg ctg cgc gta gag cct gcg gtg atg cag ggt       48
Met Gly Ala Asp Asp Thr Leu Arg Val Glu Pro Ala Val Met Gln Gly
1               5                   10                  15

ttc gcc gcg tcg ttg gat gga gcg gcc gag cat ctc gcg gtt caa ctg       96
Phe Ala Ala Ser Leu Asp Gly Ala Ala Glu His Leu Ala Val Gln Leu
            20                  25                  30

gcc gag ctg gac gct cag gtc ggg cag atg ttg ggc ggg tgg cgc ggg      144
Ala Glu Leu Asp Ala Gln Val Gly Gln Met Leu Gly Gly Trp Arg Gly
        35                  40                  45

gcg tcg ggc agt gcg tat ggc tcg gcg tgg gag cta tgg cat cgc ggg      192
Ala Ser Gly Ser Ala Tyr Gly Ser Ala Trp Glu Leu Trp His Arg Gly
    50                  55                  60

gcc ggt gag gtg cag ctg gga ttg tcg atg ctg gcg gcg gcg ata gct      240
Ala Gly Glu Val Gln Leu Gly Leu Ser Met Leu Ala Ala Ala Ile Ala
65                  70                  75                  80

cac gcc ggt gcg ggt tat caa cac aac gag acc gcg tcg gcg cag gtg      288
His Ala Gly Ala Gly Tyr Gln His Asn Glu Thr Ala Ser Ala Gln Val
                85                  90                  95

ctt cgt gag gtg ggc ggt ggc tga                                      312
Leu Arg Glu Val Gly Gly Gly
            100


<210> SEQ ID NO 31
<211> LENGTH: 103
<212> TYPE: PRT
<213> ORGANISM: M. tuberculosis

<400> SEQUENCE: 31

Met Gly Ala Asp Asp Thr Leu Arg Val Glu Pro Ala Val Met Gln Gly
 1               5                  10                  15

Phe Ala Ala Ser Leu Asp Gly Ala Ala Glu His Leu Ala Val Gln Leu
            20                  25                  30

Ala Glu Leu Asp Ala Gln Val Gly Gln Met Leu Gly Gly Trp Arg Gly
        35                  40                  45

Ala Ser Gly Ser Ala Tyr Gly Ser Ala Trp Glu Leu Trp His Arg Gly
    50                  55                  60

Ala Gly Glu Val Gln Leu Gly Leu Ser Met Leu Ala Ala Ala Ile Ala
65                  70                  75                  80

His Ala Gly Ala Gly Tyr Gln His Asn Glu Thr Ala Ser Ala Gln Val
                85                  90                  95

Leu Arg Glu Val Gly Gly Gly
            100


<210> SEQ ID NO 32
<211> LENGTH: 26
<212> TYPE: DNA
<213> ORGANISM: Artificial Sequence
<220> FEATURE:
<223> OTHER INFORMATION: Synthetic cloning primer

<400> SEQUENCE: 32

ctgagatcta tgagcctttt ggatgc                                          26
```

-continued

<210> SEQ ID NO 33
<211> LENGTH: 31
<212> TYPE: DNA
<213> ORGANISM: Artificial Sequence
<220> FEATURE:
<223> OTHER INFORMATION: Synthetic cloning primer

<400> SEQUENCE: 33
ctaagcttgg atcctcagaa cccggtatag g 31

<210> SEQ ID NO 34
<211> LENGTH: 30
<212> TYPE: DNA
<213> ORGANISM: Artificial Sequence
<220> FEATURE:
<223> OTHER INFORMATION: Synthetic cloning primer

<400> SEQUENCE: 34
ctgagatctt tgatccccgg tcggatggtg 30

<210> SEQ ID NO 35
<211> LENGTH: 30
<212> TYPE: DNA
<213> ORGANISM: Artificial Sequence
<220> FEATURE:
<223> OTHER INFORMATION: Synthetic cloning primer

<400> SEQUENCE: 35
ctcccatggg tcaggtgatc gaatcagcca 30

<210> SEQ ID NO 36
<211> LENGTH: 25
<212> TYPE: DNA
<213> ORGANISM: Artificial Sequence
<220> FEATURE:
<223> OTHER INFORMATION: Synthetic cloning primer

<400> SEQUENCE: 36
ctgagatcta tgaccatcaa ctatc 25

<210> SEQ ID NO 37
<211> LENGTH: 32
<212> TYPE: DNA
<213> ORGANISM: Artificial Sequence
<220> FEATURE:
<223> OTHER INFORMATION: Synthetic cloning primer

<400> SEQUENCE: 37
ctaagcttgg atccttaggc ccagctggag cc 32

<210> SEQ ID NO 38
<211> LENGTH: 25
<212> TYPE: DNA
<213> ORGANISM: Artificial Sequence
<220> FEATURE:
<223> OTHER INFORMATION: Synthetic cloning primer

<400> SEQUENCE: 38
ctgagatcta tgaccatcaa ctatc 25

<210> SEQ ID NO 39
<211> LENGTH: 32
<212> TYPE: DNA
<213> ORGANISM: Artificial Sequence
<220> FEATURE:
<223> OTHER INFORMATION: Synthetic cloning primer -continued

<400> SEQUENCE: 39
ctaagcttgg atcctcaggc ccagctggag cc 32

<210> SEQ ID NO 40
<211> LENGTH: 30
<212> TYPE: DNA
<213> ORGANISM: Artificial Sequence
<220> FEATURE:
<223> OTHER INFORMATION: Synthetic cloning primer

<400> SEQUENCE: 40
ctgagatctg tgcttttgcc tcttggtccg 30

<210> SEQ ID NO 41
<211> LENGTH: 27
<212> TYPE: DNA
<213> ORGANISM: Artificial Sequence
<220> FEATURE:
<223> OTHER INFORMATION: Synthetic cloning primer

<400> SEQUENCE: 41
cccaagcttc tagccggccg ccggaga 27

<210> SEQ ID NO 42
<211> LENGTH: 30
<212> TYPE: DNA
<213> ORGANISM: Artificial Sequence
<220> FEATURE:
<223> OTHER INFORMATION: Synthetic cloning primer

<400> SEQUENCE: 42
ctgagatctt tgacccacaa gcgcactaaa 30

<210> SEQ ID NO 43
<211> LENGTH: 31
<212> TYPE: DNA
<213> ORGANISM: Artificial Sequence
<220> FEATURE:
<223> OTHER INFORMATION: Synthetic cloning primer

<400> SEQUENCE: 43
ctcccatggt cactgtttcg ctgtcgggtt c 31

<210> SEQ ID NO 44
<211> LENGTH: 30
<212> TYPE: DNA
<213> ORGANISM: Artificial Sequence
<220> FEATURE:
<223> OTHER INFORMATION: Synthetic cloning primer

<400> SEQUENCE: 44
ctgagatcta tgagcggcca cgcgttggct 30

<210> SEQ ID NO 45
<211> LENGTH: 30
<212> TYPE: DNA
<213> ORGANISM: Artificial Sequence
<220> FEATURE:
<223> OTHER INFORMATION: Synthetic cloning primer

<400> SEQUENCE: 45
ctcccatggt cacggcggat caccccggtc 30

<210> SEQ ID NO 46
<211> LENGTH: 30

-continued

```
<212> TYPE: DNA
<213> ORGANISM: Artificial Sequence
<220> FEATURE:
<223> OTHER INFORMATION: Synthetic cloning primer

<400> SEQUENCE: 46

ctgagatcta tgagtttgtt ggatgcccat                                    30


<210> SEQ ID NO 47
<211> LENGTH: 30
<212> TYPE: DNA
<213> ORGANISM: Artifical sequence
<220> FEATURE:
<223> OTHER INFORMATION: Synthetic cloning primer

<400> SEQUENCE: 47

ctcccatggt taaaacccgg tgtagctgga                                    30


<210> SEQ ID NO 48
<211> LENGTH: 27
<212> TYPE: DNA
<213> ORGANISM: Artificial Sequence
<220> FEATURE:
<223> OTHER INFORMATION: Synthetic cloning primer

<400> SEQUENCE: 48

ctgagatcta tgaacgcaga ccccgtg                                       27


<210> SEQ ID NO 49
<211> LENGTH: 32
<212> TYPE: DNA
<213> ORGANISM: Artificial Sequence
<220> FEATURE:
<223> OTHER INFORMATION: Synthetic cloning primer

<400> SEQUENCE: 49

ctaagcttgg atccctagcg tgcccaagct cc                                 32


<210> SEQ ID NO 50
<211> LENGTH: 27
<212> TYPE: DNA
<213> ORGANISM: Artificial Sequence
<220> FEATURE:
<223> OTHER INFORMATION: Synthetic cloning primer

<400> SEQUENCE: 50

ctgagatcta tggttgaacc gggaagg                                       27


<210> SEQ ID NO 51
<211> LENGTH: 32
<212> TYPE: DNA
<213> ORGANISM: Artificial Sequence
<220> FEATURE:
<223> OTHER INFORMATION: Synthetic cloning primer

<400> SEQUENCE: 51

ctaagcttgg atccctatag gtcgccgccg gc                                 32


<210> SEQ ID NO 52
<211> LENGTH: 27
<212> TYPE: DNA
<213> ORGANISM: Artificial Sequence
<220> FEATURE:
<223> OTHER INFORMATION: Synthetic cloning primer

<400> SEQUENCE: 52
```

-continued

```
ctgagatcta tgtcagatca aatcacg                                  27


<210> SEQ ID NO 53
<211> LENGTH: 30
<212> TYPE: DNA
<213> ORGANISM: Artificial Sequence
<220> FEATURE:
<223> OTHER INFORMATION: Synthetic cloning primer

<400> SEQUENCE: 53

ctaagcttgg atccttagaa caagcccgcg                               30


<210> SEQ ID NO 54
<211> LENGTH: 28
<212> TYPE: DNA
<213> ORGANISM: Artificial Sequence
<220> FEATURE:
<223> OTHER INFORMATION: Synthetic cloning primer

<400> SEQUENCE: 54

ctgagatcta tggcagacac aattcagg                                 28


<210> SEQ ID NO 55
<211> LENGTH: 32
<212> TYPE: DNA
<213> ORGANISM: Artificial Sequence
<220> FEATURE:
<223> OTHER INFORMATION: Synthetic cloning primer

<400> SEQUENCE: 55

ctaagcttcc cgggtcagga tccgtggcta gc                            32


<210> SEQ ID NO 56
<211> LENGTH: 28
<212> TYPE: DNA
<213> ORGANISM: Artificial Sequence
<220> FEATURE:
<223> OTHER INFORMATION: Synthetic cloning primer

<400> SEQUENCE: 56

ctgagatcta tggatccgac cgtgttgg                                 28


<210> SEQ ID NO 57
<211> LENGTH: 25
<212> TYPE: DNA
<213> ORGANISM: Artificial Sequence
<220> FEATURE:
<223> OTHER INFORMATION: Synthetic cloning primer

<400> SEQUENCE: 57

ctgccatggt cacgaccaca taccc                                    25


<210> SEQ ID NO 58
<211> LENGTH: 26
<212> TYPE: DNA
<213> ORGANISM: Artificial Sequence
<220> FEATURE:
<223> OTHER INFORMATION: Synthetic cloning primer

<400> SEQUENCE: 58

ctgagatcta tgggtgccga cgacac                                   26


<210> SEQ ID NO 59
<211> LENGTH: 30
<212> TYPE: DNA
<213> ORGANISM: Artificial Sequence
```

-continued

```
<220> FEATURE:
<223> OTHER INFORMATION: Synthetic cloning primer

<400> SEQUENCE: 59

ctaagcttgg atcctcagcc accgcccacc                                    30
```